(12) United States Patent
Gaw

(10) Patent No.: US 10,261,023 B1
(45) Date of Patent: Apr. 16, 2019

(54) REMOTE ILLUMINATION AND DETECTION METHOD, NODE AND SYSTEM

(71) Applicant: David Curtis Gaw, Golden, CO (US)

(72) Inventor: David Curtis Gaw, Golden, CO (US)

(73) Assignee: David Curtis Gaw, Golden, CO (US)

( * ) Notice: Subject to any disclaimer, the term of this patent is extended or adjusted under 35 U.S.C. 154(b) by 413 days.

(21) Appl. No.: 14/298,784

(22) Filed: Jun. 6, 2014

Related U.S. Application Data

(60) Provisional application No. 61/896,573, filed on Oct. 28, 2013.

(51) Int. Cl.
| | |
|---|---|
| G01N 21/84 | (2006.01) |
| H05B 37/02 | (2006.01) |
| G01V 8/10 | (2006.01) |

(52) U.S. Cl.
CPC ............ *G01N 21/84* (2013.01); *G01V 8/10* (2013.01); *H05B 37/0227* (2013.01); *G01N 2201/062* (2013.01); *G01N 2201/0693* (2013.01)

(58) Field of Classification Search
CPC ............ G01N 21/84; G01N 2201/062; G01N 2201/0693; G01V 8/10; H05B 37/0227
USPC ............ 250/205, 559.12, 559.13; 340/426.2, 340/426.26, 426.27, 541, 545.3, 555, 556, 340/557; 315/158, 291, 294
See application file for complete search history.

(56) References Cited

U.S. PATENT DOCUMENTS

| | | |
|---|---|---|
| D329,825 S | 9/1992 | Taylor et al. |
| D332,459 S | 1/1993 | Morimiya |
| 6,157,317 A | 12/2000 | Walker |
| 6,774,790 B1 * | 8/2004 | Houston .............. G08B 13/183 340/539.16 |
| 7,511,612 B1 | 3/2009 | Monroe |
| D612,756 S | 3/2010 | Westra et al. |
| D653,687 S | 2/2012 | Yu |
| 8,264,167 B2 | 9/2012 | Kerr et al. |
| 8,282,480 B2 | 10/2012 | Wells et al. |
| 8,511,576 B2 | 8/2013 | Warren et al. |
| 8,544,643 B2 | 10/2013 | Yim |
| 8,571,598 B2 | 10/2013 | Valavi |
| 8,594,850 B1 | 11/2013 | Gourlay |
| D726,560 S | 4/2015 | Gaw |
| 9,401,977 B1 | 7/2016 | Gaw |

(Continued)

*Primary Examiner* — Georgia Yepps
*Assistant Examiner* — Don Williams
(74) *Attorney, Agent, or Firm* — Michael A. Kerr; Kerr IP Group, LLC

(57) ABSTRACT

A remote illumination and detection method, node, and system is described. The remote illumination and detection method generates a detection message when motion is detected by a detector. The detector includes a wireless communications module that wirelessly transmits the detection message to a remote sensing device. The remote sensing device includes a camera having a field of view and wirelessly communicates with the detector. The remote sensing device then proceeds to generate an illumination instruction to illuminate an area within the field of view, when the remote sensing device receives the detection message. The remote sensing device transmits the illumination instruction to an illuminator. The illuminator wirelessly communicates with the remote sensing device. The method then illuminates an area near the illuminator, when motion is detected by the detector and the illumination instruction is received by the illuminator.

21 Claims, 14 Drawing Sheets

(Illumination and Detection Node)

(56) References Cited

U.S. PATENT DOCUMENTS

| | | | |
|---|---|---|---|
| 2009/0322539 A1* | 12/2009 | Jeng | H05B 37/0227 340/573.1 |
| 2011/0076991 A1 | 3/2011 | Mueck et al. | |
| 2013/0074051 A1 | 3/2013 | Freeman | |
| 2014/0304317 A1* | 10/2014 | Chen | A61B 5/0015 709/201 |

* cited by examiner (Illumination and Detection Node)

(Remote Illumination Node)

(Remote Detection Node)

REMOTE ILLUMINATION AND DETECTION METHOD, NODE AND SYSTEM

CROSS REFERENCE

This patent application claims the benefit of provisional patent application 61/896,573 filed on Oct. 28, 2013 and entitled REMOTE SENSING SYSTEM UTILIZING A SMARTPHONE, which is hereby incorporated by reference in its entirety.

FIELD

The claims presented herein are related to a remote illumination and detection method, node, and system. More particularly, the claims presented herein are related to a remote illumination or detection node that is communicatively coupled to a remote sensing device.

BACKGROUND

A wide range of business, scientific, law enforcement, manufacturing, and production applications require the ability to measure and collect data and imagery in remote locations. This data supports specific operational requirements such as site security and surveillance, opening gates, measuring water or electricity levels of temperatures, as well as management reporting functions (trend information).

Remote sensing has the potential to be used in an even wider range of such applications as the value of information becomes more valuable to many industries and business areas. A limiting factor in unlocking this potential is the cost and complexity of the systems and processes required to implement remote sensing capabilities and applications. Remote sensing applications can be in fixed positions or mobile.

Remote sensing applications are diverse and extensive. Some of the applications include: water treatment, electrical power distribution and generation, oil and gas drilling and production, water management, motor racing, transportation, surveillance, military applications, environmental monitoring, scientific research, telemedicine, fishery and wildlife management and research, retail, law enforcement, energy management, testing, manufacturing, and facility and infrastructure management (e.g., bridges, tunnels and healthcare).

There is also a need and value in having remote still and video data for such functions as situational awareness, surveillance and security, alarm verification, documentation, and troubleshooting at the remote location.

Traditional remote measurement and sensing applications involve analog signals (e.g., thermistors to sense temperature) as well as digital signals (contact closures, relay outputs). Hardware for remote monitoring systems is generally purpose-designed around an embedded microprocessor, memory, modems, and IO. Modems and IO are often designed as modules in order to support configurations for different applications.

Most remote sensing applications have a requirement to operate standalone; without outside power. This is often done by solar power panels, or, increasingly, various means of energy harvesting. Remote sensing systems must be able to operate 24 hours per day, seven days per week when there is no sun, and in the case of power interruptions. Total power consumption then is a key design variable and contributes substantially to size, cost, and installation efforts. Smartphone platforms are designed for extremely low standby power consumption—often 1-2 orders of magnitude lower than traditional remote monitoring hardware.

Typical camera systems deployed for security or surveillance in outdoor settings employ motion detectors to control alarming functions, as well as the amount of video stored or transmitted. Such systems also typically employ illumination systems to enable image capture at night. Current state-of-the-art technology is a single node which integrates a camera, single or multi-sensor PIR for motion detection, and one or more illumination elements. The fields of view of the camera, passive infrared receivers (PIR), and illumination elements are designed to coincide.

There are a number of technologies for motion detection, with the most common being passive infrared receivers. Costs of perimeter surveillance systems are driven by the costs of the total number of cameras that must be deployed to cover a given area. In turn, the coverage capability of a given motion detection and illumination camera system is typically governed by the range capabilities of the motion detection and illumination components.

The overall coverage range of a given camera system has also been limited by the camera capabilities such as pixel count. As camera pixel counts have improved dramatically, the design of more cost effective perimeter surveillance systems remains limited by the reach of the motion detection and illumination components.

An improved perimeter security and surveillance solution would include an ability to detect motion over a large area at low cost, an ability to provide illumination for night imaging over a large area at low cost, and limited power requirements for both motion detection and illumination, in order to simplify cost of deployment and installation.

A system with these properties would provide a significant improvement in the price/performance capabilities of perimeter security systems by reducing the total number of cameras required to cover a given area of interest. The low power and wireless aspects provide additional improvements by lowering the total system cost by simplifying installation and maintenance of the system.

SUMMARY

A remote illumination and detection method, node, and system is described. The remote illumination and detection method generates a detection message when motion is detected by a detector. The detector includes a first wireless communications module that wirelessly transmits the detection message to a remote sensing device. The remote sensing device includes a camera having a field of view and a second wireless communications module that communicates with the first wireless communications module. The remote sensing device then proceeds to generate an illumination instruction to illuminate an area within the field of view, when the remote sensing device receives the detection message. The remote sensing device transmits the illumination instruction to an illuminator. The illuminator is communicatively coupled to a third wireless communications module that is communicatively coupled to the second communication module associated with the remote sensing device. The method then illuminates an area near the illuminator, when motion is detected by the detector and the illumination instruction is received by the illuminator. Alternatively, the detector may be communicatively coupled to the illuminator and the detector may also be configured to generate an illumination instruction that is communicated directly to the illuminator without communicating with the remote sensing device.

In an illumination and detection node embodiment, the detector and the illuminator share the same housing. Additionally, the first wireless communication module and the third wireless communications are a same wireless communication module in the illumination and detection node. The detection message is wirelessly communicated from the illumination and detection node to the remote sensing device. The area near the illuminator is illuminated when the illumination instruction communicated by the remote sensing device is received by the illumination and detection node. Another illumination and detection node embodiment enables the detector to be communicatively coupled to the illuminator, and the detector may be configured to generate an illumination instruction that is communicated directly to the illuminator without communicating with the remote sensing device.

In a remote illumination node embodiment, the illuminator is housed in a remote illuminator node that illuminates the area near the illuminator, when the illumination instruction generated by the remote sensing device is received by the remote illumination node. The remote illuminator node is an element of an illustrative remote illumination system that further includes a remote detector and a remote sensing device. The remote detector detects motion and communicates the detection message with a wireless communication protocol. The remote sensing device is communicatively coupled to the remote detector and applies the wireless communication protocol. The remote sensing device includes a camera having a field of view and a remote sensing wireless communications module that receives the detection message from the remote detector. When motion is detected and the remote sensing device receives the detection message, the remote sensing device communicates an illumination instruction to illuminate a particular area to the remote illumination node. The remote illumination node includes a remote illumination housing, a wireless network interface module, a processor, an illuminator, and a battery. The wireless network interface module is communicatively coupled to the remote sensing device. The processor receives the illumination instruction to illuminate a nearby area when motion is detected by the remote detector. The illuminator is operatively coupled to the processor and illuminates a nearby area when the illuminator receives the illumination instruction. The battery powers the illuminator, the processor, and the wireless network interface module. Alternatively, the detector may be communicatively coupled to the illuminator and the detector may also be configured to generate an illumination instruction that is communicated directly to the illuminator without communicating with the remote sensing device.

In a remote detection node embodiment, the detector is housed in a remote detection node, in which the detector that detects motion in the field of view and generates a detection message, when motion is detected. The detection message is then wirelessly communicated to the remote sensing device. The area near the illuminator is illuminated when the detection message generated by the remote detection node is received by the remote sensing device, which generates and communicates the illumination instruction to a remote illuminator node. The remote detection node includes a remote detection node housing, a wireless network interface module configured to be communicatively coupled to the remote sensing device, a detector, a processor, and a battery. The detector is operatively coupled to the processor and detects motion in the field of view. The detector also generates a detection message when motion is detected. The processor transmits a detection message that is communicated wirelessly to the remote sensing device. The battery powers the detector, the processor, and the wireless network interface module. The remote illuminator illuminates the nearby area when the detection message generated by the remote detection node is received by the remote sensing device, which then communicates the illumination instruction to the remote illuminator node. Alternatively, the detector may be communicatively coupled to the illuminator and the detector may also be configured to generate an illumination instruction that is communicated directly to the illuminator without communicating with the remote sensing device.

In a further embodiment, the illuminator includes a low power infrared LED, visible LED, IR laser, or visible laser output.

In a still further embodiment, the detector includes an infrared detector, a RF energy based detector, a sound based detector, a vibration sensor, a magnetic based sensor, an optically based motion detection system, and a beam-break sensor to detect motion across a defined light path.

In an even further embodiment, the battery is charged with a solar panel electrically coupled to the battery.

DRAWINGS

Figure 7A:
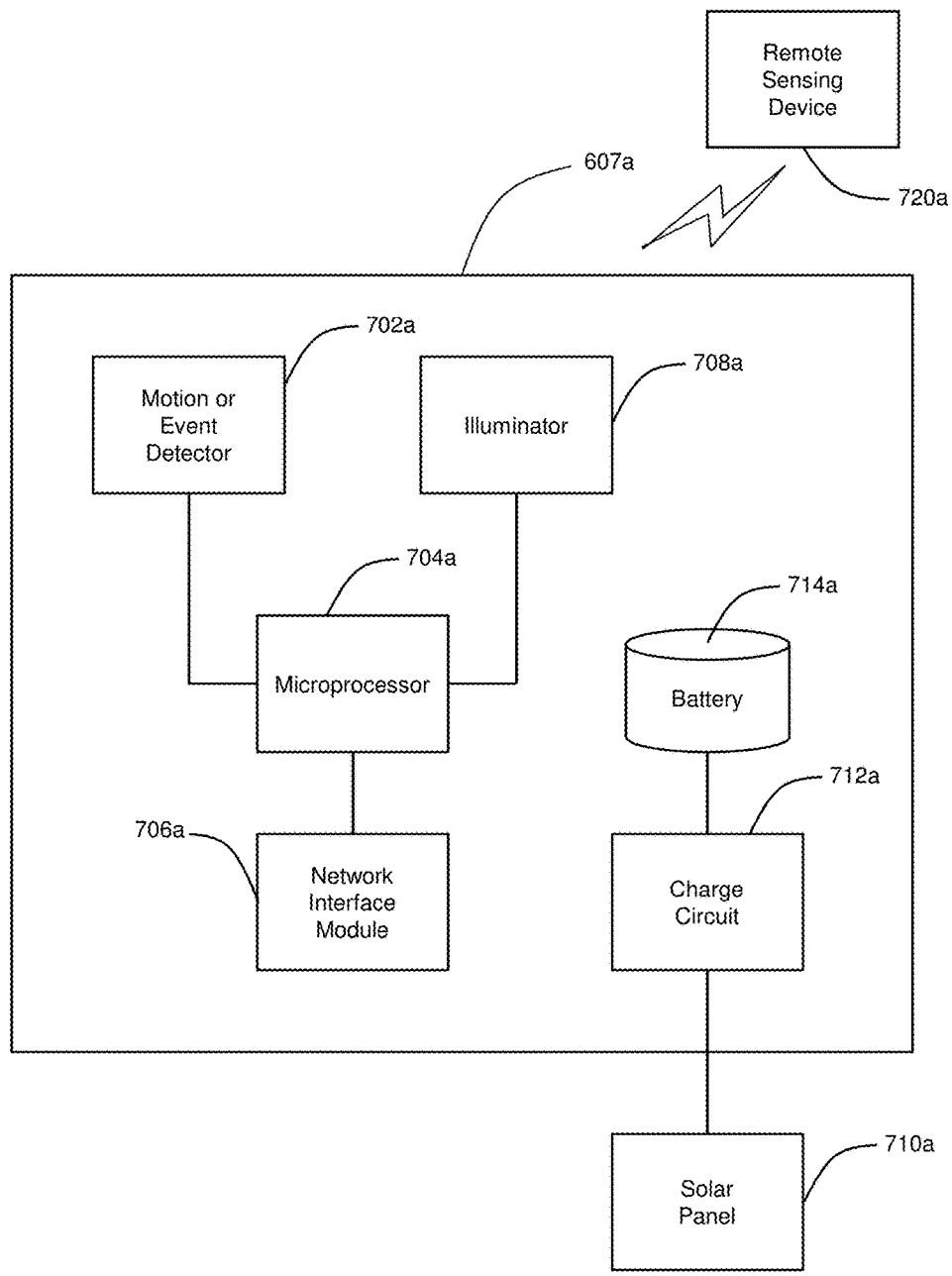
FIG. 7A shows a more detailed view of an illumination and detection node.
Figure 7B:
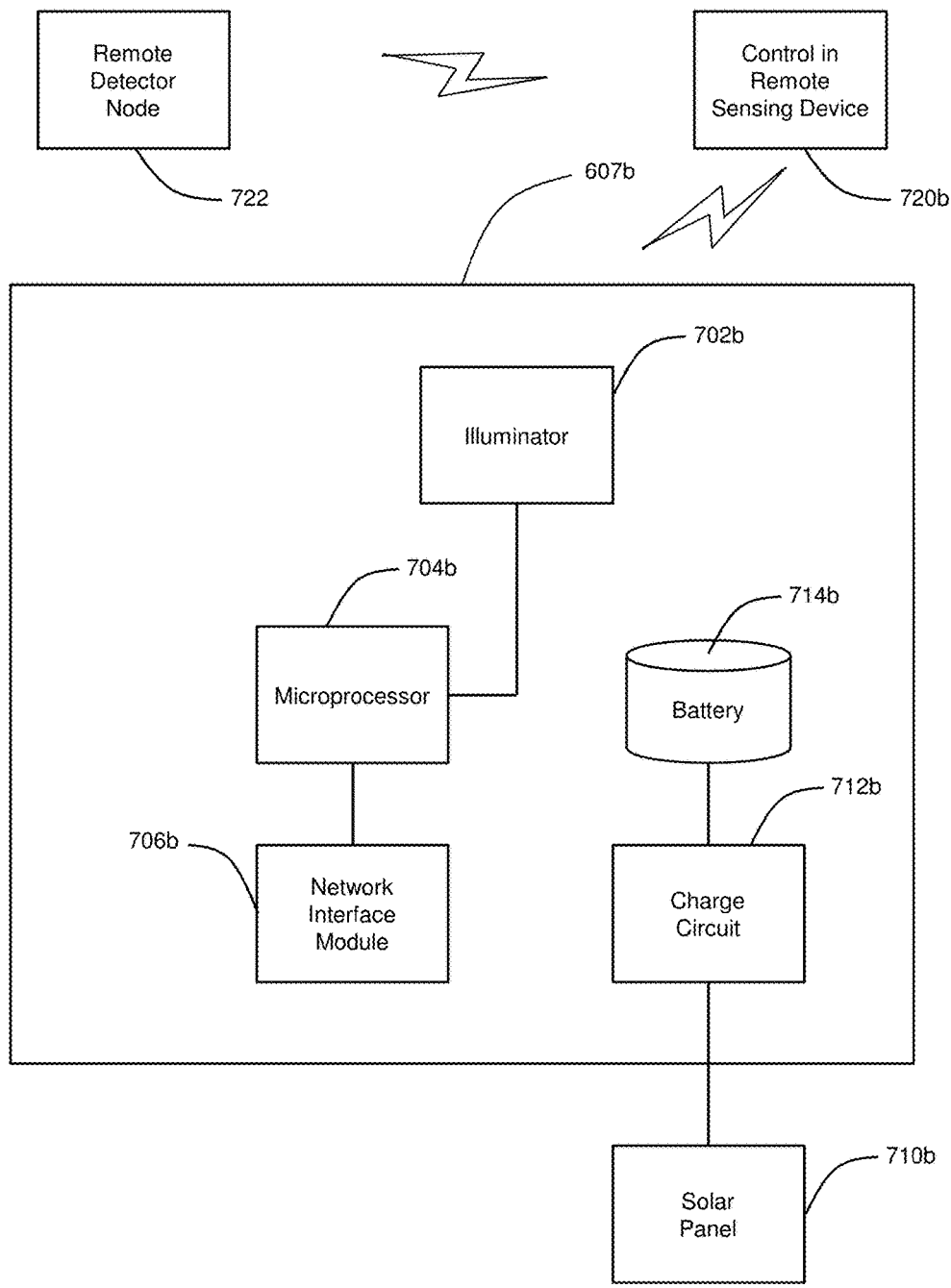
FIG. 7B shows a more detailed view of a remote illumination node.
Figure 7C:
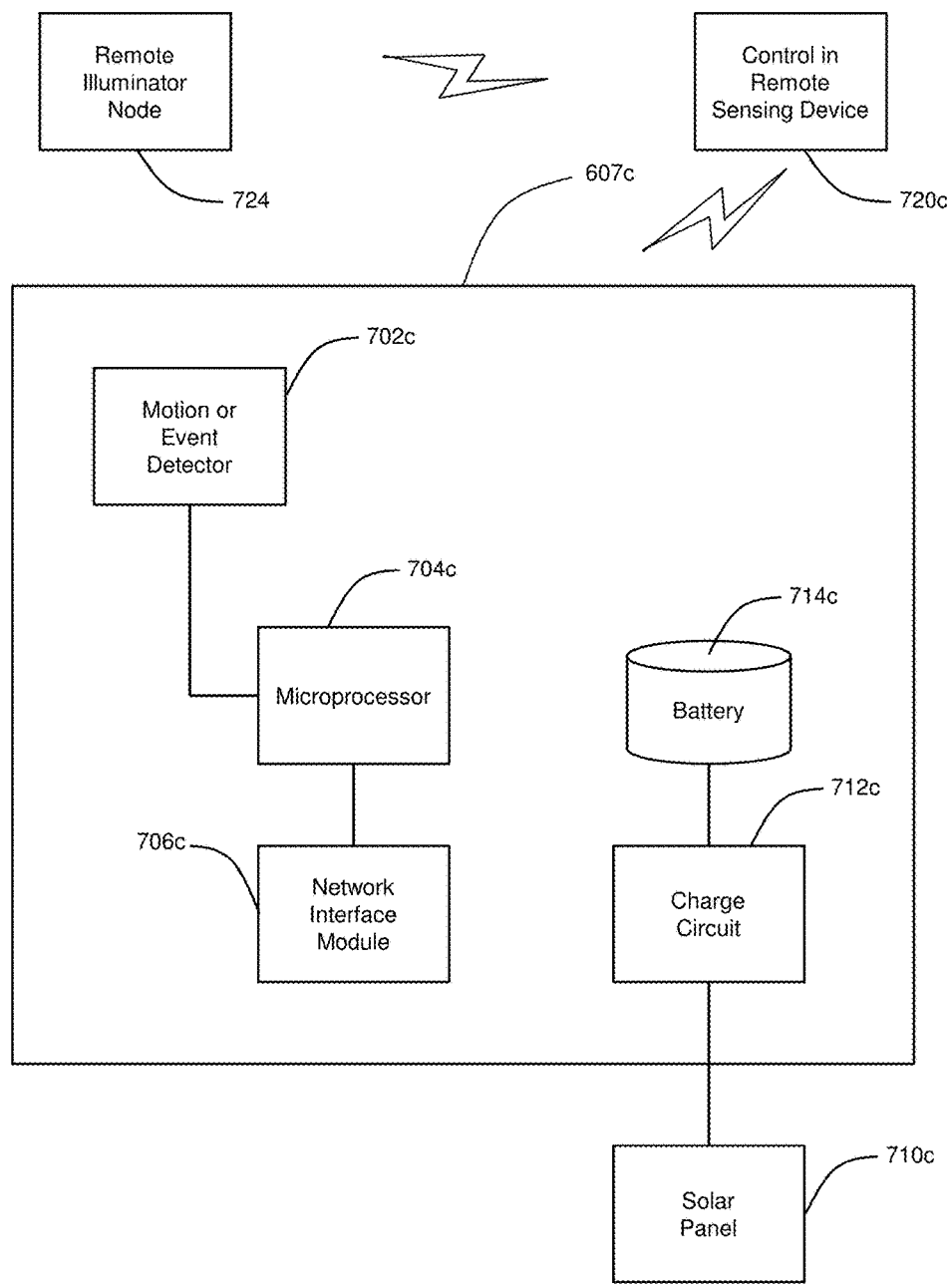

FIG. 7C shoes a more detailed view of a remote detection node.

Figure 7D:
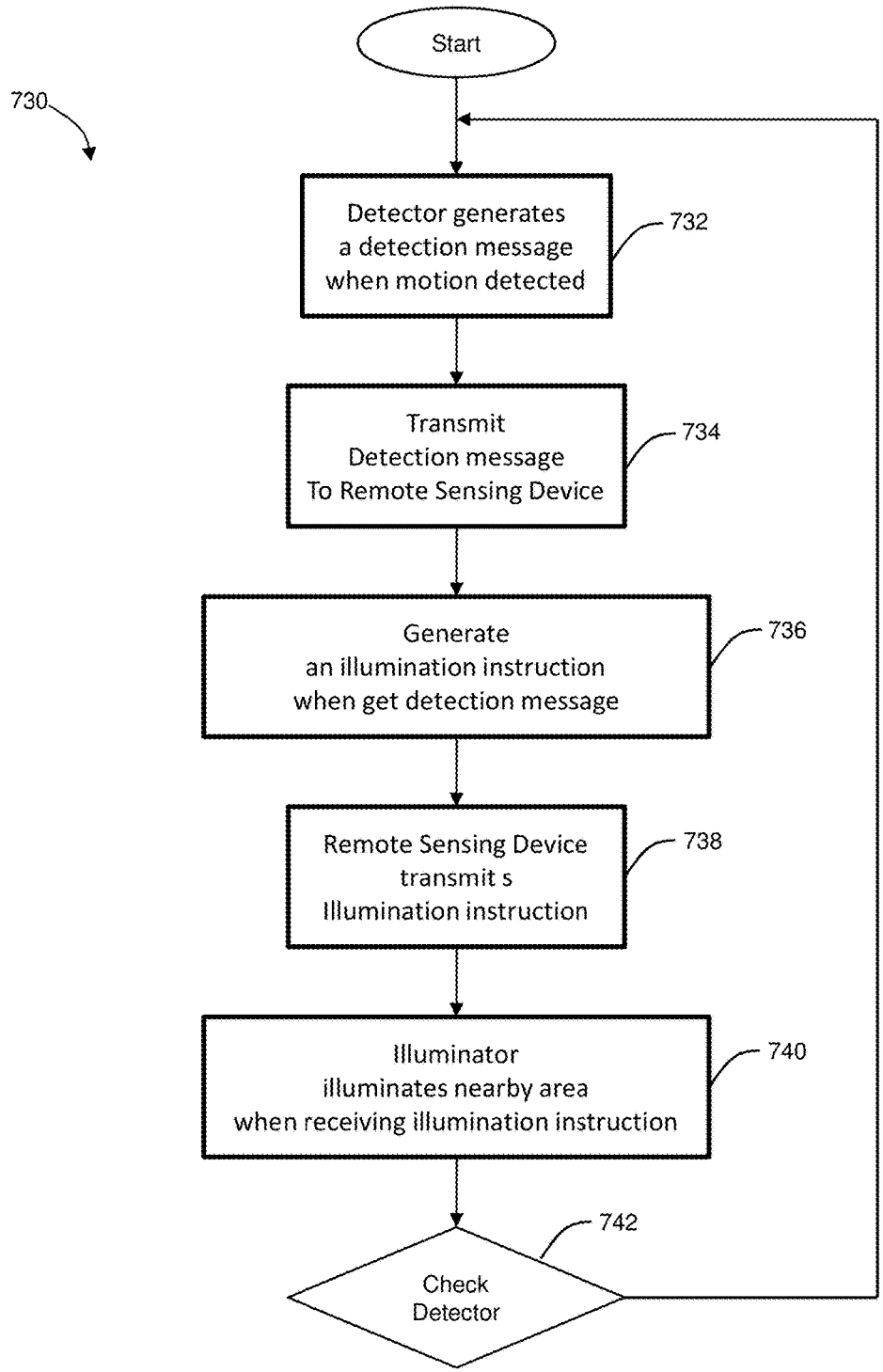

FIG. 7D shows a remote illumination and detection method.

Figure 8A:
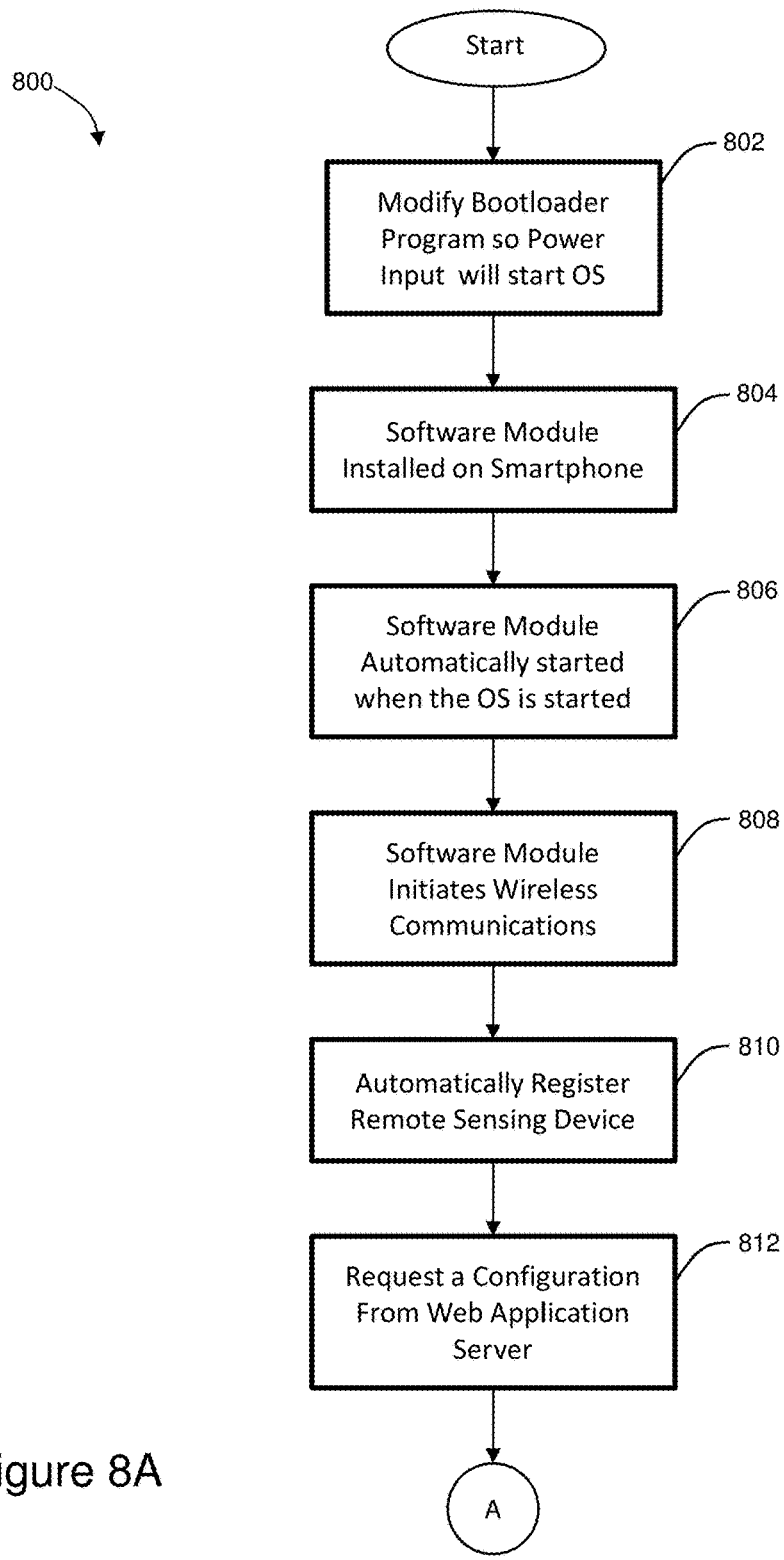
Figure 8B:
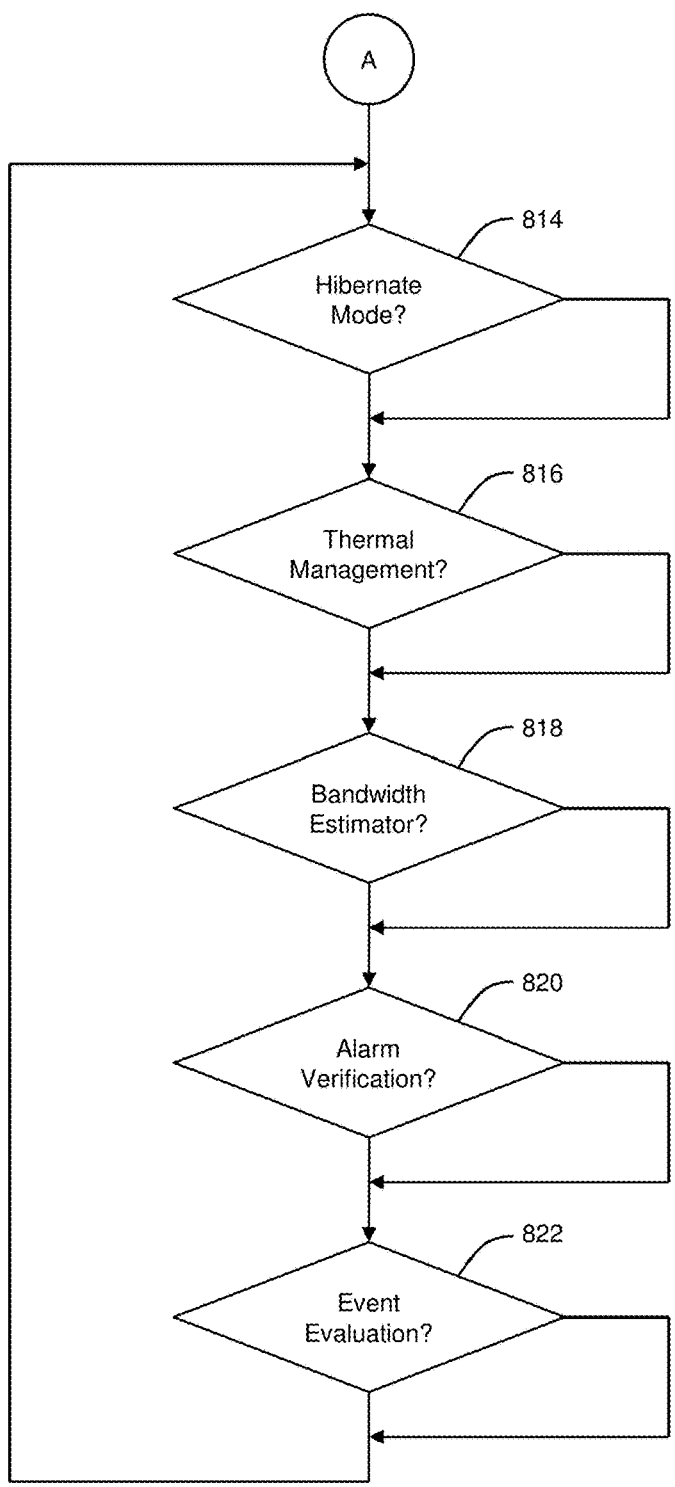

FIGS. 8A and 8B show an illustrative autonomous method for managing and controlling the remote sensing devices.

Figure 9A:
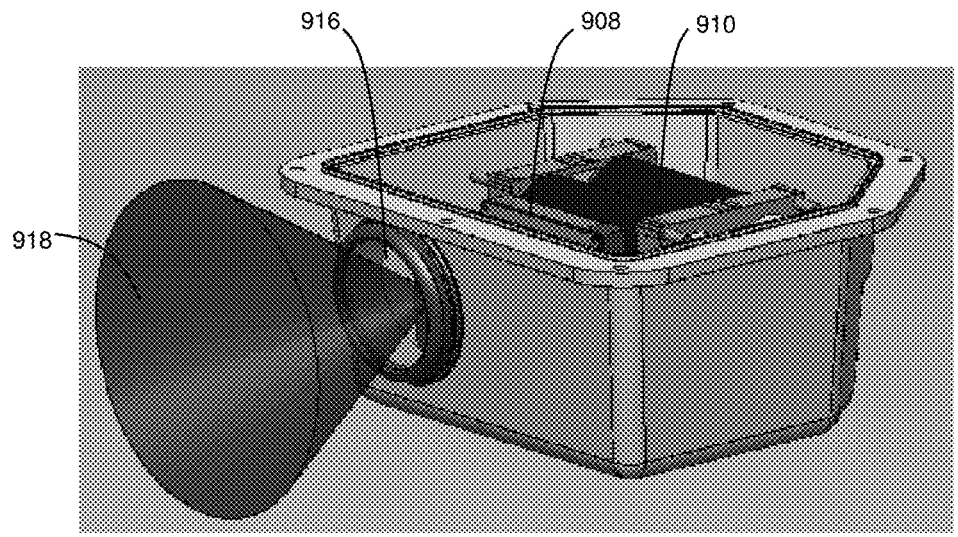

FIG. 9A shows a perspective view of an illustrative enclosure.

Figure 9B:
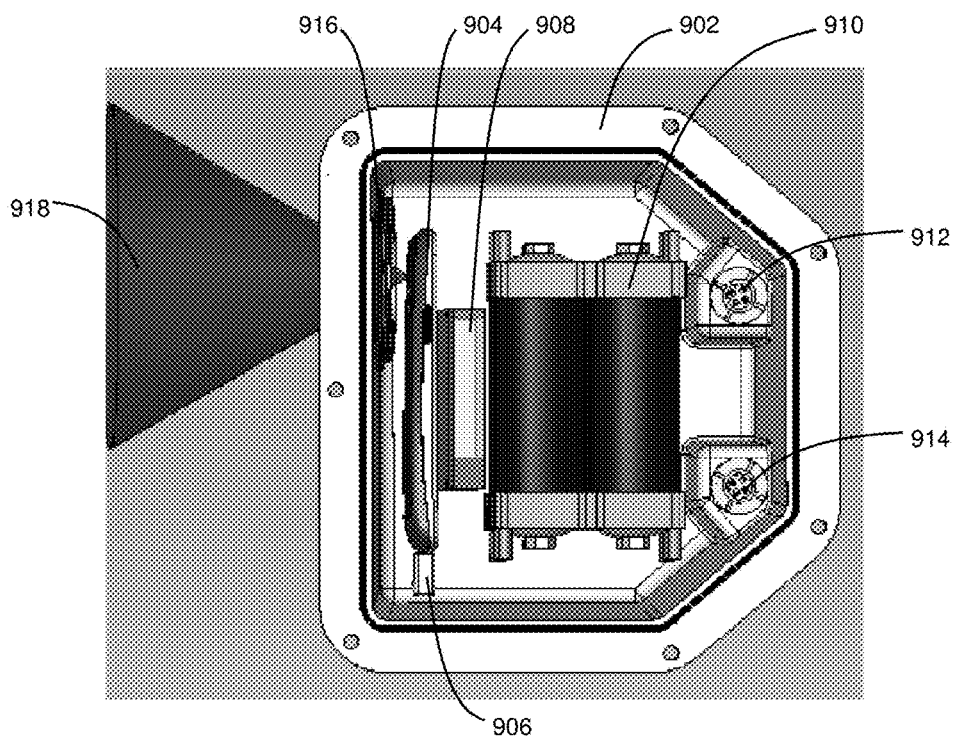

FIG. 9B shows a top view of the illustrative enclosure.

Figure 10:
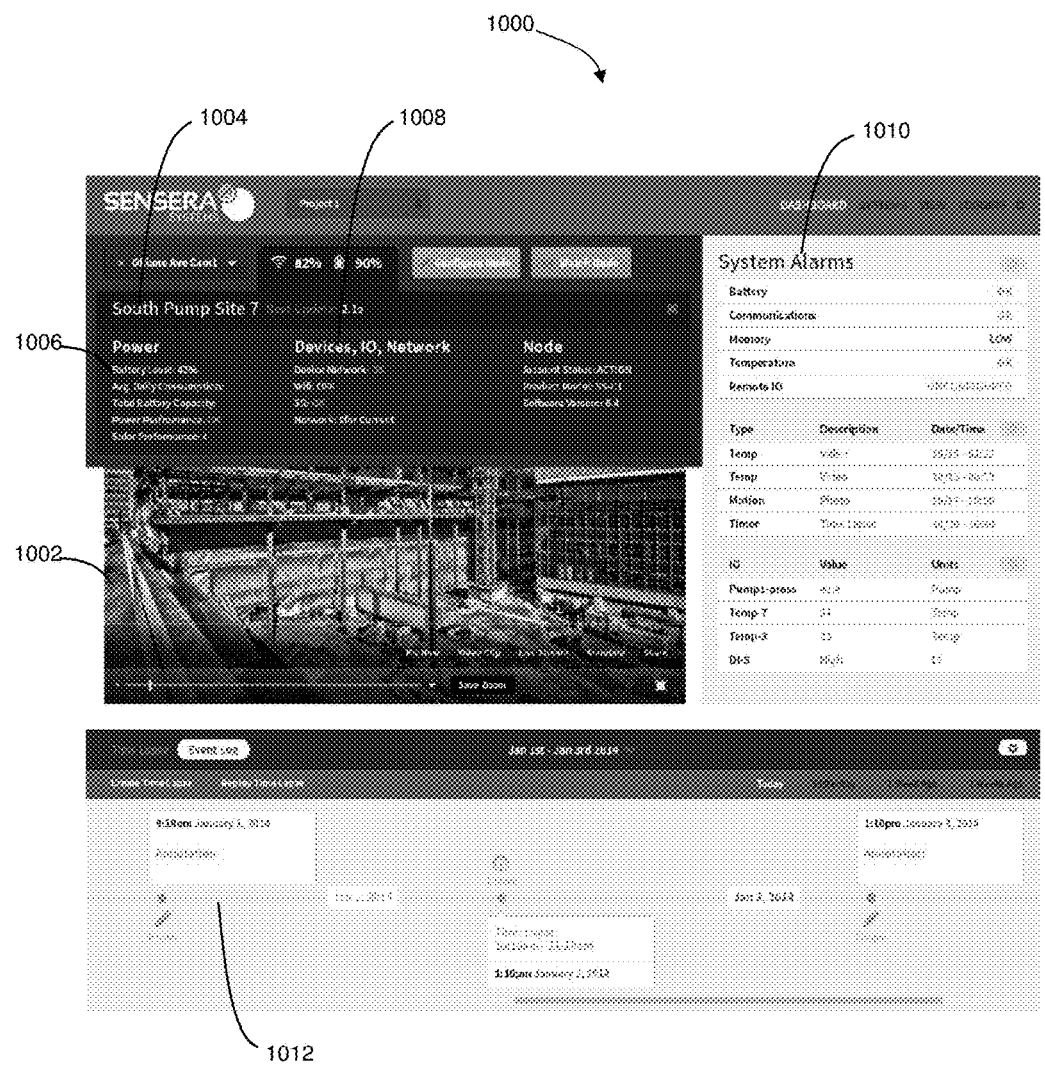

FIG. 10 shows a screenshot of an illustrative dashboard that logs data for the remote sensing system described above

DESCRIPTION

Persons of ordinary skill in the art will realize that the following description is illustrative and not in any way limiting. Other embodiments of the claimed subject matter will readily suggest themselves to such skilled persons having the benefit of this disclosure. It shall be appreciated by those of ordinary skill in the art that the systems, methods, and apparatuses described hereinafter may vary as to configuration and as to details. The systems may vary as to details and particular embodiments that reside on the network side and the elements that reside on the client side. Also, the methods may vary as to details, order of the actions, or other variations without departing from the illustrative methods disclosed here in. Additionally, the apparatuses may vary as to details such as size, configuration, mechanical elements, material properties, housings, and other such parameters.

The illustrative remote sensing device presented herein includes an enclosure with a smartphone and a microcontroller. The illustrative smartphone does not require hardware modification and supports software modification on the smartphone. Additionally, the illustrative smartphone housed by the enclosure presented herein is configured to interface with a microcontroller or circuit that is electrically coupled to the smartphone and can wirelessly communicate with a plurality of other remote sensors.

A remote sensing system that includes a network module such as an illustrative web application server is also described. In operation, the data from the remote sensors is communicated to the web application server via the microcontroller and the smartphone.

The microcontroller also communicates with a power management module that manages the power being fed from an auxiliary battery to the smartphone. The power management module manages the charging of the auxiliary battery. The power management module enables the smartphone to be powered with a sustainable, yet unreliable power source such as solar or wind power. Thus, the power management module can manage high power and low power conditions.

Smartphones are distinguished by powerful processors to handle images and video in real time including digitization of camera inputs. Also, smartphones include built-in wireless interfaces such as Wi-Fi, Bluetooth, and 3G/4G mobile. Additionally, smartphones include extremely low power consumption and various low power operation modes. Furthermore, smartphones include built-in high capacity batteries and charging circuitry, and substantial memory including non-volatile storage for large amounts of data. Further still, smartphones include multi-tasking operating systems, including the ability to easily install and configure general purpose applications which can utilize phone hardware functions including communications. Further yet, smartphones also include multi-band cellular interfaces including efficient data transmission and hardware integration including custom ASICS that provide small size, low cost, and low power consumption.

Wireless carriers have device requirements to support devices operating on their network. If hardware modifications are made to a particular smartphone, then the particular smartphone has to be recertified. In one illustrative embodiment, there are no hardware changes that require recertification.

An auxiliary battery is also provided. The auxiliary battery is electrically coupled to the power management module and the illustrative solar panels. The solar panels charge the auxiliary battery, which then charges the smartphone battery.

By way of example and not of limitation, a passive infrared (PIR) sensor or a remote thermal infrared (TIR) sensor is presented as an element of the overall system that can operate independently of the microcontroller or smartphone presented herein. The illustrative remote PIR, TIR or combination thereof is configured to interface with other camera systems.

In operation, the illustrative remote sensing system provides a perimeter security and surveillance solution that has the ability to detect motion over a large area at low cost, an ability to provide illumination for night imaging over a large area at low cost, and limited power requirements for both motion detection and illumination in order to simplify cost of deployment and installation.

The illustrative system, method, and apparatuses presented herein provide a significant improvement in the price/performance capabilities of perimeter security systems by reducing the total number of cameras required to cover a given area of interest. The low power and wireless aspects provide additional improvements by lowering the total system cost by simplifying installation and maintenance of the system. Additionally, the modifications to achieve the autonomous operation presented herein are not intended to be limiting or specific to the illustrative Android operating system. Other operating systems such as Apple's iOS, Microsoft's Windows Phone, and other such smartphone operating systems may also be used.

Illustrative features of the remote sensing device, system, and method include support for a solar powered camera, image processing including image motion detection so that video is only streamed when something happens, and alarms only when intrusion is detected. Additionally, the remote sensing system enables a remote telemetry monitoring and control system to estimate power and bandwidth consumption. Furthermore, the remote sensing system also supports thermal management over a diurnal cycle with an auxiliary battery and a clean energy source such as solar or wind.

Figure 1A:
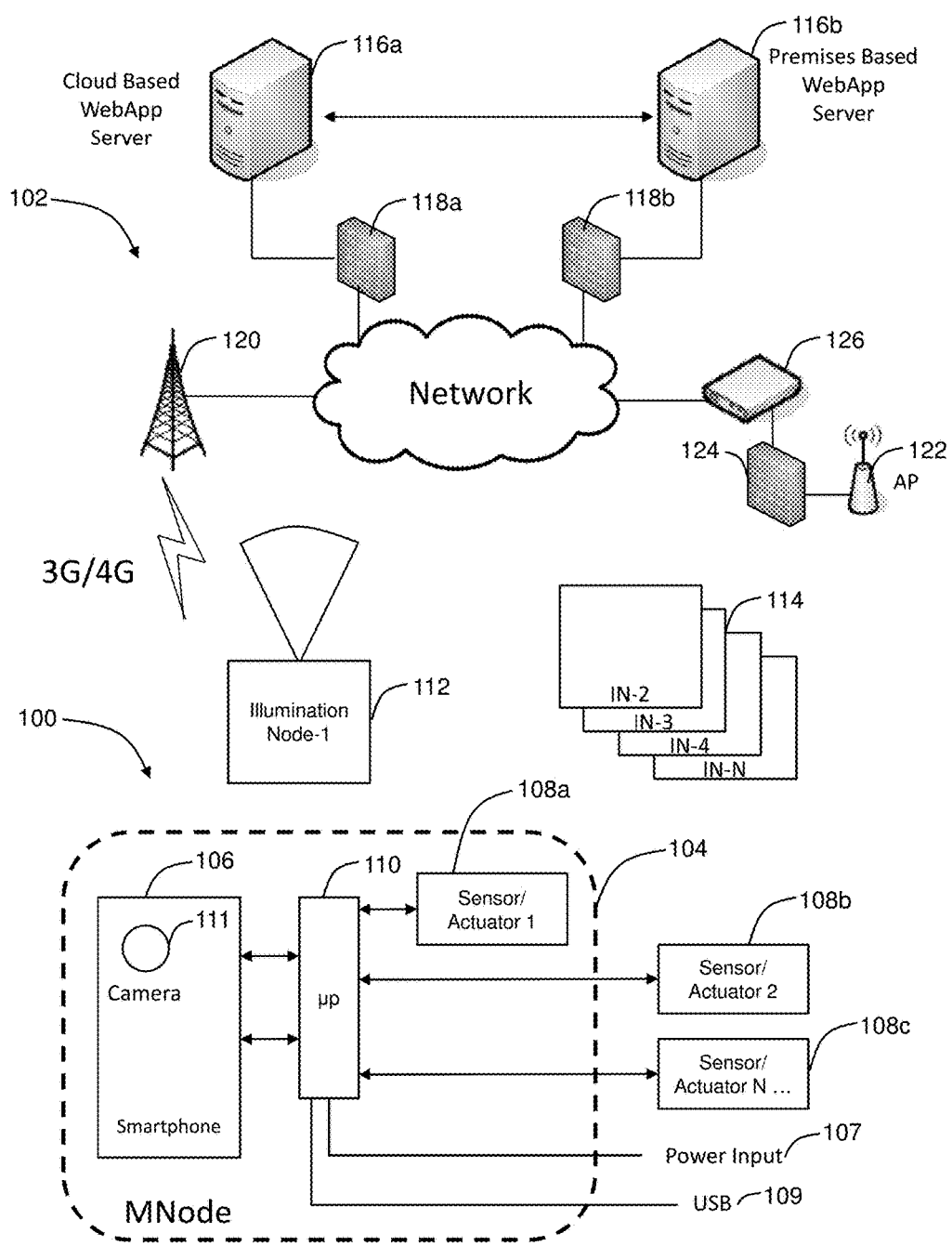
FIG. 1A shows an illustrative remote sensing device and a remote sensing system.

Referring to FIG. 1A there is shown an illustrative remote sensing device 100 and a remote sensing system 102. The illustrative remote sensing device 100 includes an enclosure 104, a smartphone 106, at least one sensor or actuator 108, and a microcontroller 110 having its own microprocessor. The illustrative remote sensing device is also referred to as an "MNode" and these terms may be used interchangeably in this patent. In the illustrative embodiment, the smartphone 106 is fixedly coupled to the enclosure 104. The illustrative smartphone 106 further includes a smartphone processor, a smartphone memory that is communicatively coupled to the smartphone processor, and a smartphone camera communicatively coupled to the smartphone processor and the smartphone memory. Further detail of the illustrative smartphone is provided in FIG. 3 below.

In one illustrative embodiment, the microcontroller 110 includes a power management module, a controller, and a wireless standard network interface. The illustrative microcontroller is electrically coupled to a power input 107, such as an auxiliary battery that is powered by a solar panel. The illustrative microcontroller is also electrically coupled to an illustrative data or communications line 109. Further detail of this illustrative embodiment is provided in FIG. 2 below.

Alternatively, the microcontroller may be more limited in its functionality and simply provide an interface for an external power supply and a battery charging circuit that is electrically coupled to the smartphone 106, as described in FIG. 1B below.

By way of example and not of limitation, the illustrative sensor or actuator 108 includes a motion detection sensor 108a that signals when motion is detected and then triggers the smartphone camera 111 to capture at least one image. The illustrative motion sensor 108a may be within the enclosure 104. In an alternative embodiment, the motion sensor 108a may also be external to the enclosure and be communicatively coupled to the microcontroller using the WSN, Wi-Fi, NFC, a hardwired connection such as USB or Ethernet, and any other such communication methods or standards.

To allow imaging at night or during low light with the smartphone camera 111 sensor, the illustrative remote sensing system may also include at least one illumination node 112. Additionally, a plurality of illumination nodes 114 may be utilized to further extend the viewing range of the smartphone camera 111. The illumination nodes may be strategically located within the physical premises. Additionally, the illumination may occur inside the enclosure.

Figure 5:
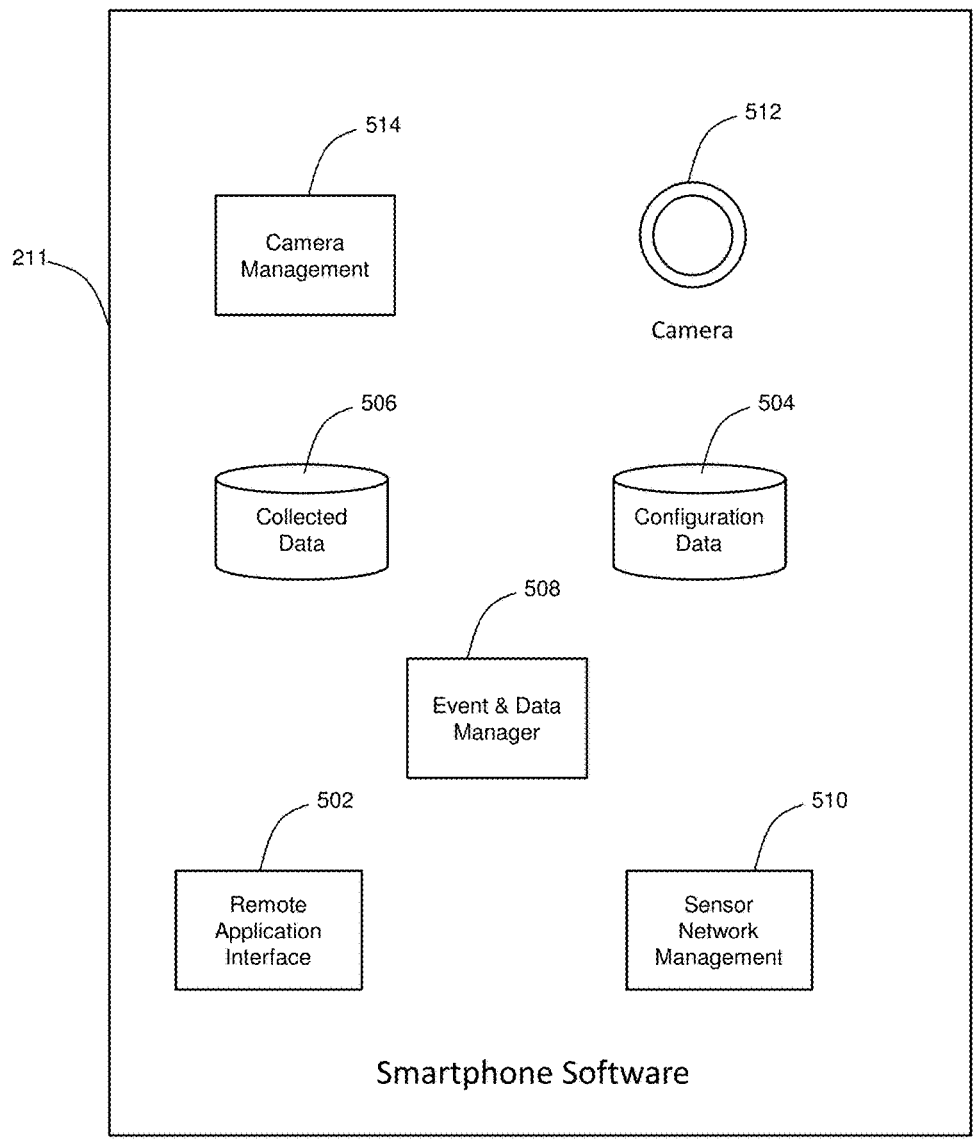
FIG. 5 shows the illustrative software components for the remote sensing device and system.
Figure 6:
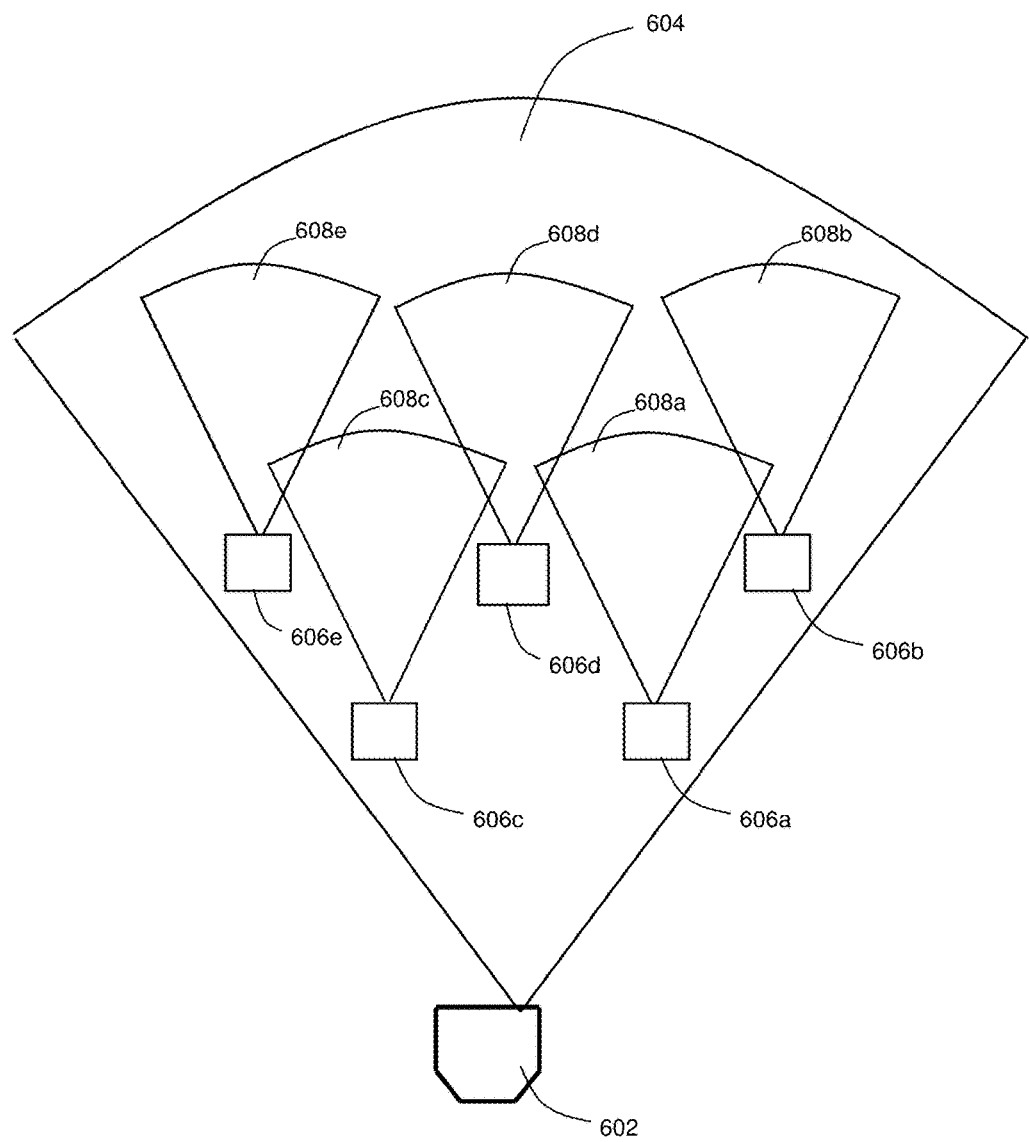
FIG. 6 shows the combination of a remote sensing device and a sensor illumination node.

In one illustrative embodiment, the illustrative sensor 108 includes a daylight sensor that indicates when it is dark and causes the illumination node 112 to illuminate a nearby area so the smartphone camera can capture an illuminated image. Further detail of the illustrative illumination node is provided in FIGS. 5 and 6 presented below.

In a further embodiment, the remote sensing device may also include a sensor 108b or 108c that is separated from the enclosure. The illustrative separate sensor 108b includes a separate camera communicatively coupled to the smartphone 106 and a separate motion detection sensor 108c that signals when motion is detected and sends a message using one of the smartphone communication interfaces to the separate camera, which then captures at least one image. By way of example and not of limitation, the separate sensor 108b may be disposed inside the enclosure 104.

In a still further embodiment, the sensor 108 within the remote sensing device may also include a temperature sensor 108a. The temperature sensor 108a may be used to control a cooling component and a heating component that is described in further detail in FIG. 2 below.

The remote sensing device 100 is communicatively coupled to a networked module 116, which includes by way of example and not of limitation an illustrative web application server 116. In one embodiment the web application server 116a is disposed in a network cloud. In another embodiment the web application server 116b is disposed on a premises based server. In certain embodiment, the network may be a hybrid that includes the premises based server 116b and the cloud based server 116a.

The illustrative cloud based web application server 116a and premises based web application server 116b are both behind an illustrative hardware firewall 118a and 118b, respectively. Alternatively, communications with the web applications servers may be performed using a virtual private network (VPN) that does not require a hardware firewall and operates as a "software" firewall. In one illustrative embodiment, the network communications include wirelessly communicating with an illustrative base station 120 that is managed by a wireless carrier. Alternatively, communications with the remote sensing device include an illustrative Wi-Fi access point 122 that operates behind a software or hardware firewall 124, which is communicatively coupled to a modem 126 that, in turn, is communicatively coupled to the Internet.

The illustrative network module 116 includes a database that receives the sensor signal output and corresponding timestamp. The timestamp may be generated by the sensor, the smartphone, or other network device in the communications path between the sensor or actuator 108 or smartphone 106 and the network module 116. In another illustrative embodiment, the database is communicatively coupled to the networked module and logs the sensor signal output and timestamp communicated by the smartphone 106 or sensor 108.

By way of example and not of limitation, the illustrative network module for the remote sensing system includes a web application server that further includes the database. Additionally, the smartphone of the remote sensing system further includes a smartphone application that configures the smartphone to interface with the illustrative microcontroller 110. In alternative embodiment, the smartphone includes at least one Application Programming Interface (API) that receives the sensor signal output, and the API communicates the sensor signal output received by the smartphone to the database associated with the web application server.

In yet another embodiment, a power input 107 interfaces with input power gathered from an external source such as mains, solar panel, energy harvesting circuits, and other such power sources. One or more actuators 108 may be connected to the remote sensing device via wired or wireless interfaces, such as Ethernet, serial, Wi-Fi, Bluetooth, 802.15.4, Zigbee, or other low-power wireless sensing network interface. The remote sensing device 100 communicates with sensors to read sensed values, as well sensor configuration data. The remote sensing device 100 communicates with actuators to set output values. An illustrative USB 109 communications port, such as USB2, allows the remote sensing device 100 to receive user inputs and provide user feedback.

Figure 1B:
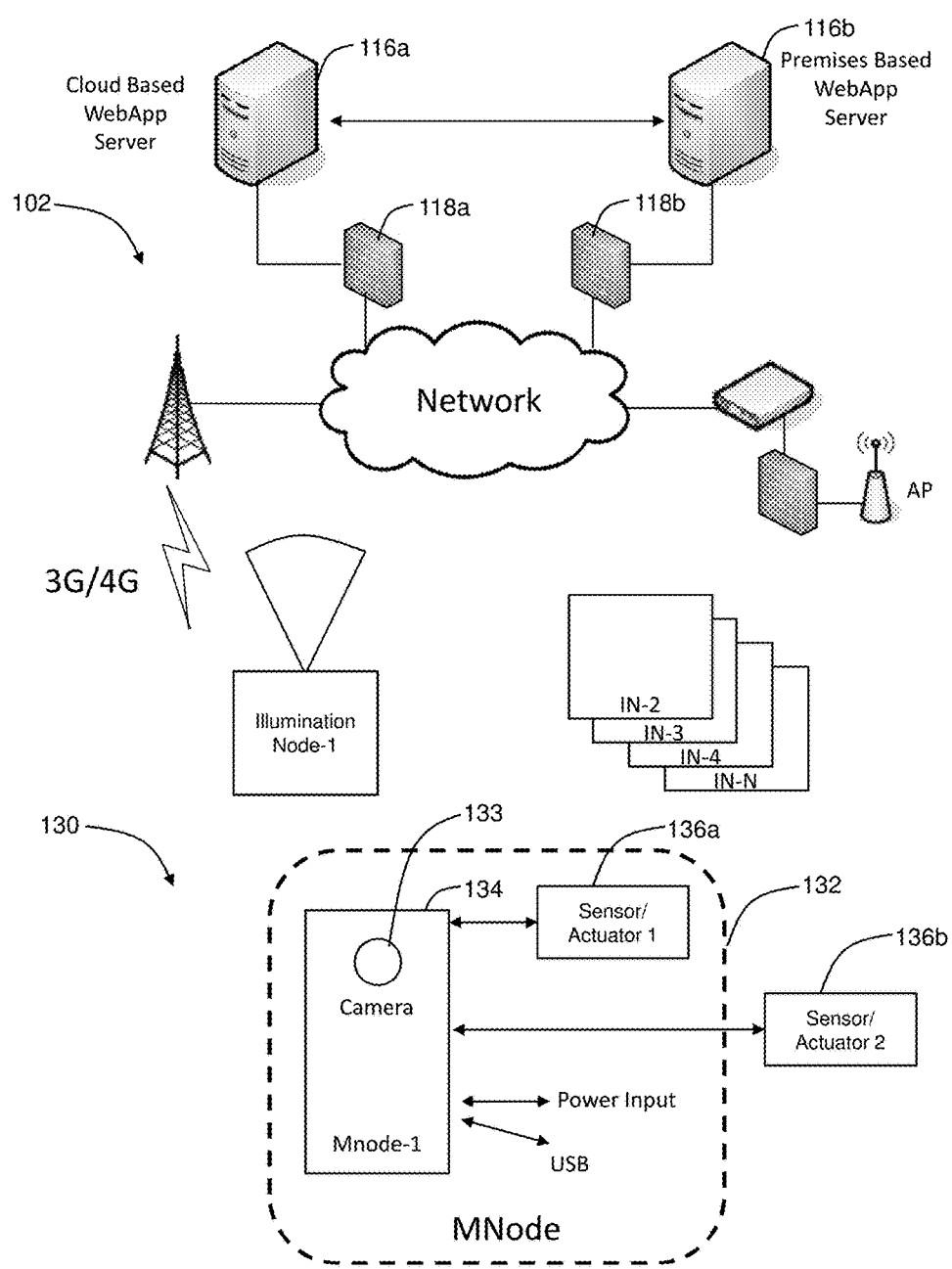
FIG. 1B shows an alternative illustrative remote sensing device that operates in similar manner as the remote sensing device in FIG. 1A.

Referring to FIG. 1B there is shown an alternative illustrative remote sensing device 130 that operates in similar manner as the remote sensing device 100, except without the microcontroller 110. The remote sensing device 130 includes an enclosure 132, a smartphone 134, and at least one sensor or actuator 136. As described herein, the smartphone is fixedly coupled to the enclosure and includes a smartphone processor, a smartphone memory, smartphone battery, and a smartphone camera communicatively coupled to the smartphone processor and the smartphone memory.

In one illustrative embodiment, the smartphone camera 133 operates as an internal sensor that captures at least one image. The smartphone 134 generates a corresponding timestamp. The image and timestamp are then communicated to wide area network.

In another illustrative embodiment, the sensor 136a is housed within the enclosure 132, and the sensor 136a is electrically coupled and communicatively coupled to the smartphone 134 via the second smartphone network interface. Alternatively, the sensor or actuator 136 may include an external sensor 136b that housed outside in the enclosure 132 and is separately powered, yet communicatively coupled to the smartphone 134.

In operation, at least one of the sensors 133, 136a, or 136b detects at least one sensor signal output and communicates the sensor signal output to the smartphone 134, which then communicates the sensor signal output and a corresponding timestamp to the wide area network. As presented above, the remote sensing device 130 is communicatively coupled to a networked module, which includes by way of example and not of limitation an illustrative web application server 116. In one embodiment the web application server 116a is disposed in a network cloud and in another embodiment the web application server 116b is disposed on a premises-based server. The illustrative cloud based web application server 116a and premises-based web application server 116b are both behind an illustrative hardware firewall 118a and 118b, respectively. Alternatively, communications with the web applications servers may be performed using a virtual private network (VPN) that does not require a hardware firewall and operates as a "software" firewall.

The illustrative web application server 116 may also be embodied as one of four fundamental cloud service models, namely, infrastructure as a service (IaaS), platform as a service (PaaS), software as a service (SaaS), and network as a service (NaaS). The cloud service models are deployed using different types of cloud deployments that include a public cloud, a community cloud, a hybrid cloud, and a private cloud.

Infrastructure as a service (IaaS) is the most basic cloud service model. IaaS providers offer virtual machines and other resources. The virtual machines, also referred to as instances, are run as guests by a hypervisor. Groups of hypervisors within the cloud operational support system support large numbers of virtual machines and the ability to scale services up and down according to customers' varying requirements. IaaS clouds often offer additional resources such as images in a virtual machine image library, raw (block) and file-based storage, firewalls, load balancers, IP addresses, virtual local area networks (VLANs), and software bundles. IaaS cloud providers supply these resources on demand from their large pools installed in data centers. For wide area connectivity, the Internet can be used or virtual private networks (VPNs) can be used.

Platform as a service (PaaS) enables cloud providers to deliver a computing platform that may include an operating system, a programming language execution environment, a database, and a web server. Application developers can develop and run their software solutions on the PaaS without the cost and complexity of buying and managing the underlying hardware and software layers. With some PaaS solutions, the system resources scale automatically to match application demand so that the cloud end user does not have to allocate resources manually.

Software as a service (SaaS) enables cloud providers to install and operate application software in the cloud. Cloud end users access the software from cloud clients. The cloud end users do not manage the cloud infrastructure and platform that run the application. The SaaS application is different from other applications because of scalability. Scalability can be achieved by cloning tasks onto multiple virtual machines at run-time to meet the changing work demand. Load balancers in the SaaS application distribute work over a set of virtual machines. To accommodate a large number of cloud end users, cloud applications may be multitenant and serve more than one cloud end user organization. Some SaaS solutions may be referred to as desktop as a service, business process as a service, test environment as a service, communication as a service, etc.

The fourth category of cloud services is Network as a service (NaaS), in which the capability provided to the cloud service end user is to use a network/transport connectivity services, an inter-cloud network connectivity services, or the combination of both. NaaS involves the optimization of resource allocations by considering network and computing resources as a unified whole, and traditional NaaS services which include flexible and extended VPN and bandwidth on demand.

In addition to the smartphone 100 and smartphone 130, other "cloud" clients may access the networked module 116. These client devices include, but are not limited to, desktop computers, laptops, tablets, and other smartphones. Some of these cloud clients rely on cloud computing for all or a majority of their applications, and would be essentially useless without it. Many cloud applications do not require specific software on the client device and instead use a web browser to interact with the cloud application.

There are different types of cloud deployment models for the cloud-based service, which include a public cloud, a community cloud, a hybrid cloud, and a private cloud. In a public cloud, applications, storage, and other resources are made available to the general public by a service provider. These services are free or offered on a pay-per-use model.

The community cloud infrastructure is between several organizations from a community with common concerns, whether managed internally or by a third-party and hosted internally or externally; so the costs are spread over fewer users than a public cloud (but more than a private cloud).

The private cloud infrastructure is operated solely for a single organization, whether managed internally or by a third-party and hosted internally or externally. A private cloud project requires virtualizing the business environment, and it requires that the organization reevaluate decisions about existing resources.

The hybrid cloud is a composition of two or more clouds (private, community, or public) that remain unique entities but are bound together, offering the benefits of multiple deployment models. Hybrid cloud architecture requires both on-premises resources and off-site (remote) server-based cloud infrastructure. Although hybrid clouds lack the flexibility, security, and certainty of in-house applications, a hybrid cloud provides the flexibility of in-house applications with the fault tolerance and scalability of cloud-based services.

The illustrative network module 116 may operate in any of the cloud service or cloud infrastructure models presented herein or which may readily suggest themselves to those of ordinary skill in the art having the benefit of this patent. The three primary software applications for the remote sensing system 102 include the smartphone 106 software module, the illustrative web application server 116 software module, the microcontroller 110 firmware module, and firmware running in any of the remote sensors or actuators.

The illustrative smartphone 106 software module includes a local software module configured to be executed on the smartphone 106. By way of example and not of limitation, a smartphone using the Android operating system is configured to run a software application that communicates with the illustrative web application server 116 software module.

The illustrative smartphone 106 software module is also configured to receive configuration parameters from the web application server 116, which control the operation of the remote sensing device 100 or 130. These configuration parameters allow programming the remote sensing device 100 or 130 to schedule when logged data in the remote sensing device 100 or 130 software module is uploaded to the management node for archival and/or viewing. The control parameters also include the frequency the smartphone 106 software module should contact the illustrative web application server 116 that is configured to retrieve any pending commands. The control parameters also include "events" or a schedule that cause an image, a video, or an analog or digital input to be captured by the remote sensing device 100 or 130. An illustrative analog or digital input includes a Passive Infrared (PIR) motion detection input. Another control parameter includes conditions to test for generating alarms, such as an alarm caused by PIR triggering. Yet another control parameter includes sending a destination and at least one message for each condition that occurs.

The illustrative web application server 116 software module includes a web-based application that executes in the cloud and communicates with all registered remote sensing devices 100 or 130. The illustrative web application server 116 software module is also configured to archive data from the remote sensing devices 100 or 130 and provide end users with a graphical interface for interacting with the remote sensing devices.

As described herein, the illustrative web application server 116 may reside in the cloud and include a mirror of collected data, controls for setting configuration and managing multiple remote devices, controls to deal with billing based on device, controls for billing data access, network usage, controls to deal with end sensor device network management include sensor device registration, and automating device configuration such as carrier based service limits. In yet another illustrative embodiment, the illustrative web application server 116 may also operate as a distributed system.

The illustrative microcontroller 110 firmware module performs power management supervision, alarming, wireless sensor node management, and manages environmental controls that provide heating and/or cooling. The illustrative microcontroller 110 firmware module communicates with the smartphone 106 software module via USB. In an alternate embodiment, the illustrative microcontroller 110 firmware module is configured to communicate with the smartphone 106 software module with a wireless communication protocol such as Wi-Fi, NFC, or Bluetooth.

Figure 2:
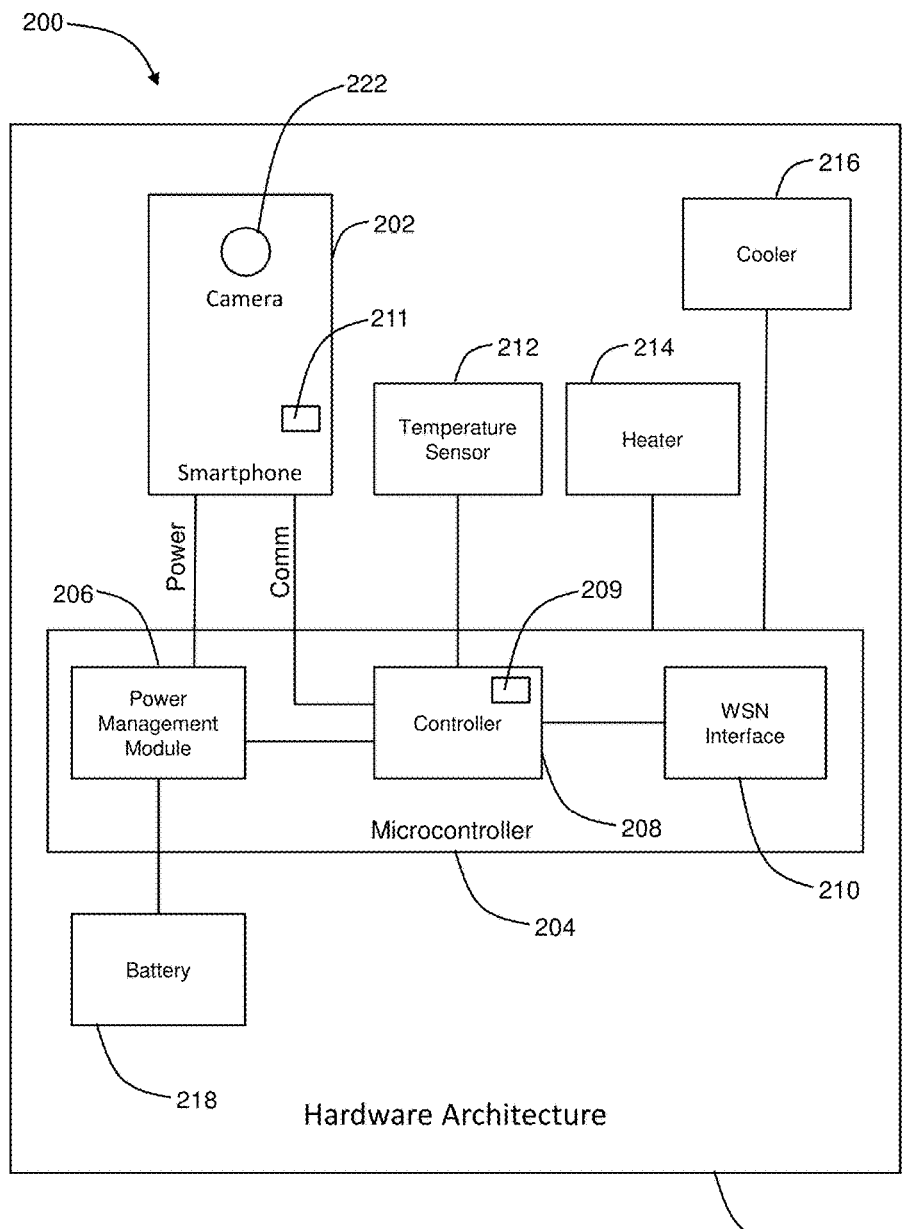
FIG. 2 shows a detailed view of another illustrative remote sensing device and the associated hardware components.

Referring to FIG. 2, there is shown a detailed view of another illustrative remote sensing device 200 and the associated hardware components. An illustrative smartphone 202 executes the smartphone 106 software module and performs remote sensing, alarming, and data archival. The illustrative remote sensing device 200 comprises a microcontroller 204 that further includes a power management module 206, a controller 208, a wireless sensor network (WSN) interface 210, a temperature sensor 212 such as a thermistor operatively coupled to the microcontroller, a cooler element 216, and a heater element 214 that are also communicatively coupled to the microcontroller 204. The microcontroller 204 includes a wireless sensor network (WSN) 210 interface that can operate with additional wireless standards that are not supported by the smartphone 202.

The controller 208 includes a microcontroller firmware module 209, which manages and controls power management processes including reporting battery level, alarming devices at threshold levels, and communicating with wireless sensor nodes using the wireless sensor network 210. Specific input events received by the controller 208 notify the smartphone to perform a particular operation. For example, the microcontroller firmware module 209 may be triggered to take a picture when a motion detector fires. In another illustrative example, the microcontroller firmware module 209 may be triggered to maintain the temperature within the enclosure 220 within a required temperature range that keeps the smartphone 202 working properly.

Additionally, the illustrative microcontroller firmware 209 includes code that executes on the controller 208 and performs power management supervision, alarming, wireless sensor node management, and environmental controls operations such as heating and cooling. In the illustrative embodiment, the microcontroller firmware module 209 communicates with the smartphone software module 211 via USB. In an alternative embodiment, the microcontroller firmware module 209 communicates with the smartphone software module 211 via a wireless interface such as NFC, Bluetooth, or Wi-Fi.

Additionally, the WSN interface 210 is configured to interface with one or more remote sensors or other such Input/Output devices that can communicate using the WSN interface 210. This allows remote inputs to be read by the remote sensing device 200.

In operation, the illustrative power management module 206 provides input power conditioning of the external power input and battery charging circuitry, feeding both the internal smartphone battery and the auxiliary battery 218 with a charge signal. The controller 208 communicates with the power management module 206 and is configured to turn the smartphone 202 on or off.

An enclosure 220 houses the smartphone 202, electronic circuit 204, temperature sensor 212, cooler 216, and heater 214. This enclosure 202 seals these components from the environment and provides an appropriate thermal environment which can be temperature controlled to maintain internal temperatures within allowable range in the face of ambient temperature fluctuations. In the illustrative embodiment, the enclosure 220 is fabricated from materials that do not attenuate RF signals in the bands used by cellular, Wi-Fi, Bluetooth, NFC, and wireless sensor networks.

In the illustrative embodiment, the microcontroller 204 connects to the smartphone with a USB connection. In the illustrative embodiment, the ADB protocol is used with the USB connection in order to allow the microcontroller 204 to communicate with the smartphone 202 in a flexible fashion. Other protocols for communicating over a USB serial link or alternative wireless link embodiment may also be employed.

The smartphone software module 211 executing on the smartphone 202 is configured to communicate with the microcontroller 204 over USB, thereby allowing the phone 202 to have access to power management functions, as well as nodes attached to the WSN. Other modes and protocols for communication between the microcontroller 204 and the smartphone 202 will be apparent to one skilled in the art.

In certain embodiments, the smartphone 202 may be fitted with an optional external lens to provide narrower field of view or dynamic zoom capabilities. Additionally, the remote sensing device 200 may include an electro-mechanical mechanism that enables the remote sensing device to point itself (and correspondingly, the camera field of view) within a larger overall field of regard using a pan-tilt mechanism. This pan-tilt mechanism may be controlled by the remote sensing device 200 based on locally-executing logic, or based on events detected by the attached WSN nodes, or based on remote user inputs.

The cooling component 216 within the enclosure 220 cools the smartphone and the sensors housed by the enclosure when the temperature rises above a first threshold temperature that is measured by the temperature sensor. The heating component within the enclosure heats the smartphone and/or the sensors and/or the batteries housed by the enclosure when the temperature falls below a second threshold temperature that is measured by the temperature sensor.

In operation, the controller 208 communicates control signals to the smartphone 202. The controller 208 controls the power management module 206 and decides whether to feed power to the smartphone or not. Thus, the controller optimizes power management by enabling the smartphone to enter and exit a sleep mode. In one illustrative embodiment, the smartphone software module 211 includes a power logic module and the microcontroller 204 includes a separate power logic module, in which the microcontroller 204 may decide to put the smartphone in sleep mode. The controller 204 also regulates the internal temperature of the enclosure so that the phone does not overheat or get too cold.

The power management module 206 performs battery charging operations and state of charge measurements for the auxiliary battery 218 and for the smartphone 202. The power management module 206 includes a battery charging circuit that charges the auxiliary battery 218. The power management module includes a high power mode and a low power mode. The controller also manages the power being fed from the auxiliary battery 218 to the smartphone 202. The power management module 206 manages the charging of the auxiliary battery 218. The power management module 206 enables the smartphone to be powered with a sustainable, yet unreliable power source such as solar or wind power. Thus, the power management module can manage high power and low power conditions.

The operations of the microcontroller 204 may also be performed by the smartphone processor, smartphone memory, and smartphone wireless transceivers communicatively to the local sensors. In that case, the illustrative smartphone would have to be powered with a typical 5V power connection. Current smartphones support Wi-Fi, Bluetooth and NFC and can use these wireless communication standards to communicate with other sensors. The smartphone may be powered with solar panel adapters that provide the required 5V charging power for a smartphone.

Figure 3:
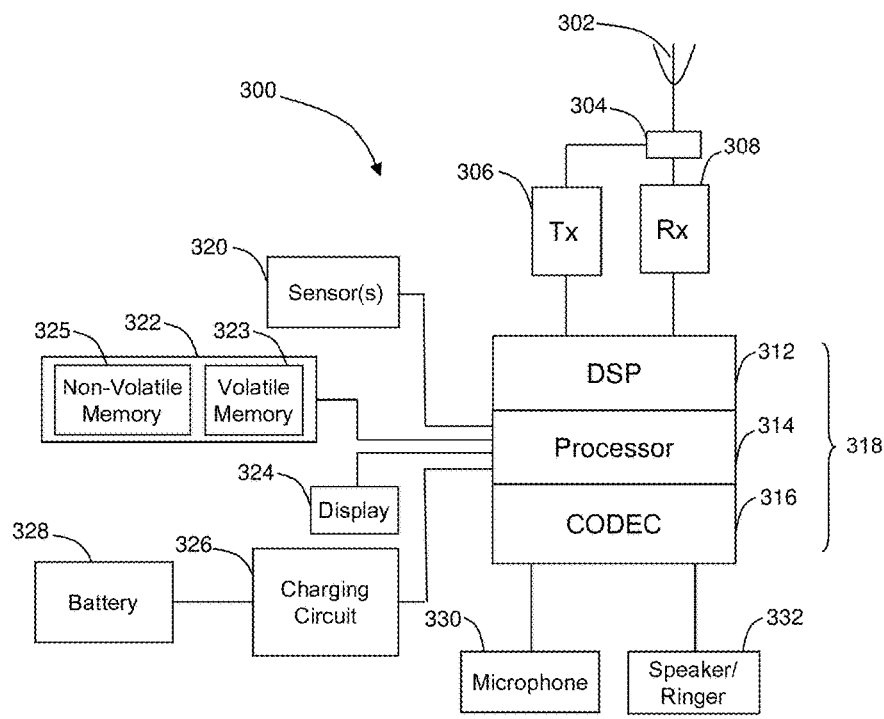
FIG. 3 shows the electrical components for an illustrative smartphone.

Referring to FIG. 3, there is shown the electrical components for an illustrative smartphone 300. For purposes of this patent, the illustrative smartphone 300 is a multimode wireless device that comprises a first antenna element 302 that is operatively coupled to a duplexer 304, which is operatively coupled to a multimode transmitter module 306, and a multimode receiver module 308.

An illustrative control module 318 comprises a digital signal processor (DSP) 312, a processor 314, and a CODEC 316. The control module 318 is communicatively coupled to the transmitter 306 and receiver 308. The transmitter module and receiver module are typically paired and may be embodied as a transceiver. The illustrative transmitter 306, receiver 308, or transceiver is communicatively coupled to antenna element 302.

The DSP 312 may be configured to perform a variety of operations such as controlling the antenna 302, the multimode transmitter module 306, and the multimode receiver module 308. The processor 314 is operatively coupled to a sensor 320, such as a camera. In operation, the camera sensor 320 is configured to be managed and controlled by the smartphone processor.

The processor 314 is also operatively coupled to a memory 322, a display 324, and a charging circuit 326. The charging circuit is operatively coupled to a smartphone battery 328.

Additionally, the processor 314 is also operatively coupled to the CODEC module 316 that performs the encoding and decoding operations and is communicatively coupled to a microphone 330 and a speaker 332. The CODEC module 316 is also communicatively coupled to the display 324 and provides the encoding and decoding operations of captured video.

The memory 322 includes two different types of memory, namely, volatile memory 323 and non-volatile memory 325. The volatile memory 323 is computer memory that requires power to maintain the stored information, such as random access memory (RAM). The non-volatile memory 325 can retain stored information even when the wireless communication device 300 is not powered up. Some illustrative examples of non-volatile memory 325 include flash memory, ROM memory, and hard drive memory.

Smartphone 300 may also be referred to as a mobile handset, mobile phone, wireless phone, portable cell phone, cellular phone, portable phone, a personal digital assistant (PDA), a tablet, a portable media device, a wearable computer, or any type of mobile terminal which is regularly carried by an end user and has all the elements necessary for operation in the remote sensing system. The wireless communications include, by way of example and not of limitation, 3G, 4G, LTE, CDMA, WCDMA, GSM, UMTS, or any other wireless communication system such as wireless local area network (WLAN), Wi-Fi or WiMAX. Additionally, the smartphone 300 may also be connected via USB (or via the Microcontroller) to an external Satellite modem in order to provide an alternative to Mobile or Wi-Fi for WAN connection.

Figure 4:
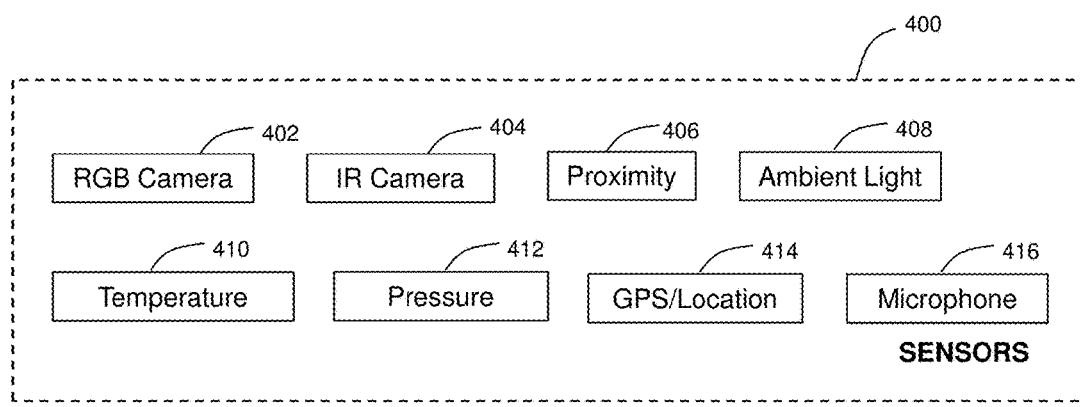
FIG. 4 shows a plurality of illustrative sensors that may be operatively coupled to the smartphone, microcontroller, or any combination thereof.

Referring to FIG. 4, there is shown a plurality of illustrative sensors 400 that may be operatively coupled to the smartphone, microcontroller, or combination thereof. The sensors include an RGB camera 402 that may be used to capture images, videos, or any combination thereof. Another sensor includes an infrared (IR) camera 404 the may be used to capture IR images, IR videos, or any combination thereof. A proximity sensor 406 may be used to detect a person entering a particular location, and the proximity sensor 406 may operate using an IR sensor. An ambient light sensor 408 or photo sensor detects changes in light, and the changes in light may be generally associated with a responsive input. A temperature sensor 410 detects the temperature, which may be generally associated with a responsive input. A pressure sensor 412 detects the pressure and is generally associated with a responsive input, e.g. change in pressure may indicate change in weather. A GPS or location sensor 414 may also be used to determine or provide the location of smartphone, microcontroller or any combination thereof. Also, a microphone 416 may be utilized as a sound sensor. Additionally, auxiliary sensors for connecting to smartphones are known in the art; these illustrative sensors take the form of a "sled" or phone "case" that incorporates a sensor that is not available inside the smartphone, e.g. a thermal camera. Such a smartphone "peripheral" can easily be incorporated and provide an additional sensor in the system.

FIG. 5 shows the illustrative software components for the remote sensing device and system described herein. The illustrative software components 211 are configured to be executed within the standard operating system framework on the smartphone hardware described above. In the illustrative embodiment, at least one the software components 211 is configured to communicate with the microcontroller described herein. Typical operating system services and resources are available to the software modules and enable them to execute functions as required, and to access system resources such as the camera and non-volatile memory.

The first component of the software architecture includes the remote application interface module 502 which manages the interaction with the remote user and any remote management application. More specifically, the remote application interface module 502 is configured to communicate with the illustrative WebApp Server 116 (shown in FIG. 1). The remote application interface module 502 processes commands for changing the configuration data 504, retrieves the collected data 506, and receives immediate readings from attached sensors or the camera. The illustrative remote application interface is also responsible for sending any alarms or notifications generated by event and data manager 508.

The illustrative collected data component 506 includes an illustrative database store of data acquired from the camera and/or any attached sensors collected by the configuration data 504 specification.

The illustrative configuration data component 504 includes parameters that relate to the configuration of the remote sensing system, including configurable aspects of data collection. By way of example and not of limitation, data collection parameters include specification of the conditions upon which to begin and end data collection for each point, the frequency of sampling, etc. These conditions may have programmatic meaning because they are based on values of other sampled data. For example, the camera can be trigged to store an image or a video clip when an attached motion detector is activated.

The illustrative configuration data component 504 also includes a specification for events and notifications based in measured values from attached sensors and camera(s). By way of example and not of limitation, an alarm can be set such that if an attached temperature sensor reads above a certain value, then an email, text message, or phone call is made to the specified addresses.

In the illustrative embodiment, a sensor network management module 510 is configured to communicate with any sensors attached to or communicatively coupled to the remote sensing system.

An illustrative event and data manager 508 module is configured to ensure data is collected according to configuration data component 504. Additionally, the event data manager 508 is further configured to generate alarms and notifications according to configuration data component 504. The event and data manager 508 also provides analytics. The event data manager 508 includes logic to detect events based on collected data. For example, one illustrative embodiment is a video motion detection function that utilizes video or images from the camera to determine if there is motion present in the scene. Such motion would result in a motion detection event, which may then be communicated or used to trigger other events or actions."

In the illustrative embodiment, the integrated camera 512 may be connected to an optional lens that is integral with the enclosure and the camera/enclosure mounting system. The illustrative camera 512 can be accessed from the smartphone operating system in order to capture still images or video clips. Depending on the smartphone used, the camera may also include flash or other auxiliary mechanism to enhance image quality under various conditions.

In an alternative embodiment, an optional second camera communicates with the smartphone via Wi-Fi or other short-range wireless technology supported by the smartphone (NFC, Bluetooth, etc.) The smartphone controls the auxiliary camera to configure, capture images/video, etc. as if the auxiliary camera were built into the smartphone. Images from the external camera are transferred over the wireless interface to the smartphone and then are treated as if they were captured from the smartphone's internal camera.

The illustrative camera management module 514 manages the integrated and optional auxiliary cameras to capture still or video imagery based on commands from the event and data manager 508, and then stores those captured images in the collected data 506.

The smartphone software components 211 are configured to operate at very low power. All programmed events (such as timed data logging and schedules for upload of data) are analyzed, and the smartphone software application utilizes operating system features to place the phone into low power mode. Low power mode is exited when either the timer has expired, or a message has arrived from the microcontroller over USB, indicating an urgent IO event has occurred.

In one illustrative embodiment, an algorithm operating on the microcontroller reads the thermistor and controls the heater and cooler to maintain internal temperature within operating range of the smartphone.

FIG. 6 shows the combination of a remote sensing device and a sensor illumination node, which may be used as a perimeter security system. The illustrative remote sensing device 602 includes one of the remote sensing devices presented above and the corresponding hardware and software architecture.

In FIG. 6, the illustrative remote sensing device 602 includes a camera having a field of view 604. During the day, the sunlight provides enough light to fully illuminate the field of view of the camera of the remote sensing device 602.

However, at night, a single light source is unable to illuminate the entire field of view 604. To better illuminate the entire field of view 604, a plurality of sensor illumination nodes 606 are used. Each sensor illumination node 606 includes a sensor and an illuminator that provides a sensor illumination field of view 608. For example, the sensor illumination nodes 606a, 606b, 606c, 606d and 606e have a corresponding sensor illumination field of view 608a, 608b, 608c, 608d and 608e, respectively.

In operation, each sensor illumination node 606 senses motion or other events of interest in the vicinity of that particular sensor illumination node 606. When the sensor illumination node 606 detects an event, the particular sensor illumination node 606 sends a message to the remote sensing device 602 using the illustrative wireless sensor network. The remote sensing device may then instruct the particular sensor illumination node 606 to turn on the illumination so that imagery can be captured at night or with increased fidelity. The sensor illumination nodes 606 are closer to the event or subject of interest than just a remote sensing device. As a result, a larger area can be covered by the wirelessly networked sensor nodes, in spite of sensing range limitations and illumination range limitations associated with the sensor illumination nodes 606.

Referring to FIGS. 7A, 7B and 7C there is shown a remote illumination and detection node, a remote illumination node, and a remote detection node, respectively. More generally, a remote illumination and detection method 730 is also shown in FIG. 7D.

The illustrative remote illumination and detection method 730 is initiated at block 732 where a detector generates a detection message when motion is detected by the detector. The illustrative detector includes a first wireless communications module that wirelessly transmits the detection message to a remote sensing device as described in block 734.

At block 736, the remote sensing device then proceeds to generate an illumination instruction to illuminate an area within the field of view, when the remote sensing device receives the detection message. The illustrative remote sensing device includes a camera having a field of view and a second wireless communications module that communicates with the first wireless communications module associated with the detector. The first wireless communications module and the second wireless communications module use the same wireless communication protocol.

The method then proceeds to block 738 where the remote sensing device transmits the illumination instruction to an illuminator. The illuminator is communicatively coupled to a third wireless communications module that is communicatively coupled to the second communication module associated with the remote sensing device.

At block 740, an area near the illuminator is illuminated, when motion is detected by the detector and the illumination instruction is received by the illuminator.

Referring now to FIG. 7A, there is shown an illustrative illumination and detection node 607a that is communicatively coupled to the remote sensing device 720a. The illumination and detection node 607a embodiment includes a motion or event detector 702a and an illuminator 708a that share the same housing, a microprocessor 704a, and network interface module 706a. The illustrative illumination and detection node 607a share a network interface module that includes at least one wireless communication module that operates using a wireless communication protocol such as WSN, Wi-Fi, Bluetooth, NFC, and other such wireless communications standards.

In operation, the detector 702a generates the detection message when motion is detected. The detection message is wirelessly communicated from the illumination and detection node 607a to the remote sensing device 720a. The remote sensing device 720a may then proceed to generate an illumination instruction, which is then communicated to the illumination and detection node 607a. The area near the illuminator 708a is illuminated when the illumination instruction communicated by the remote sensing device 720a is received by the illumination and detection node 607a. The illuminator may remain on until another illumination instruction is received that instructs the illuminator to turn off. The illumination and detection node 607a includes a battery 714a electrically coupled to a charge circuit 712a that is electrically coupled to a solar panel 710a. Alternatively, power may be provided from other energy sources such as a gasoline or diesel generator, the electrical grid, wind energy and other such energy sources.

Referring to FIG. 7B, there is shown an illustrative remote illumination system that includes an illumination node 607b communicatively coupled to a remote sensing device 720b, which in turn is communicatively coupled to a remote detector 722. An illuminator 702b is housed within the remote illuminator node 607b that illuminates the area near the illuminator 702b. The illumination node 702b is communicatively coupled to remote sensing device 720b which is communicatively coupled to remote detector 722. When the remote detector 722 detects motion, a detection message is generated that is communicated to the remote sensing device 720b using a wireless communication protocol. The remote sensing device includes a camera having a field of view and a remote sensing wireless communications module that receives the detection message from the remote detector. The remote sensing device then determines whether to generate an illumination message. For example, the illumination message may be generated when it is dark or there is a power outage or other such event that would require illuminating the area near the illuminator and within the field of view of the remote sensing device 720b camera.

The remote illumination node 607b includes a remote illumination housing, a wireless network interface module 706b, a processor 704b, the illuminator 702b, and a battery 714b electrically coupled to a charge circuit 712b. In the illustrative embodiment the charge circuit 712b is electrically coupled to a solar panel 710b. The wireless network interface module 706b is communicatively coupled to the remote sensing device 720b. The processor 704b receives the illumination instruction to illuminate a nearby area when motion is detected by the remote detector 722. The illuminator 702b is operatively coupled to the processor and illuminates a nearby area when the illuminator 702b receives the illumination instruction. The illuminator may remain on until another illumination instruction is received that instructs the illuminator to turn off. The battery 714b powers the illuminator 702b, the processor 704b and the wireless network interface module 706b.

Referring to FIG. 7C, there is shown a remote detection node 607c communicatively coupled to remote sensing device 720c, which communicates with remote illuminator 724. The remote detection node 607c houses a motion or event detector 702c that detects motion in the field of view of the remote sensing device 720c. When motion is detected by the remote detection node 607c, a detection message is generated and communicated to the remote sensing device 720c. The area near the illuminator 724 is illuminated when the detection message generated by the remote detection node 607c is received by the remote sensing device 720c, and the remote sensing device 720c determines that an illumination instruction must be generated and communicated to the remote illuminator node 724. The illuminator may remain on until another illumination instruction is received that instructs the illuminator to turn off.

The remote detection node 607c includes a housing, a wireless network interface module 706c communicatively coupled to the remote sensing device 720c, a detector 702c, a processor 704c and a battery 714c. The battery 714c is electrically coupled to a charge circuit 712c, which is electrically coupled to a solar panel 710c. The motion or event detector 702c is operatively coupled to the processor 704c and detects motion in the field of view of the camera corresponding to the remote sensing device 720c. The detector 702c generates a detection message, when motion is detected. The detection message is communicated wirelessly to the remote sensing device 720c. The battery powers the detector, the processor and the wireless network interface module.

By way of example and not of limitation, the illuminator 708a, 702b and 724 may include a low power infrared or visible LED or laser output. Additionally, the illustrative detector 702a, 722, and 702c may include an infrared detector, RF-based motion sensor, a vibration-based motion sensor, a light-beam based presence sensor, or an optically-based motion detection module (e.g. camera that includes image processing).

In operation, a person walking across the detection field of the illustrative motion or event detector 702a, 722 and 702c would be detected. When it is dark, the illustrative remote sensing devices 720a, 720b and 720c sends a signal to the illuminator 708a, 702b, and 724, respectively, to illuminate a nearby area. The signal to the illuminator may be sent after a specific delay time that models the time required for the illumination instruction generated by the remote sensing device to be sent, received, and acted upon. The illuminator 708a, 702b, and 724 then illuminates the scene for a particular period of time that allows the remote sensing device 720a, 720b and 720c, respectively, to complete its image acquisition.

In another embodiment, a day/night sensor automatically turns on the illuminator when motion is detected at night time, and then sends a message to the remote sensing device. In yet another embodiment, the detector 702a, 722 and 702c includes an infrared detector having a low power design system that is excited by incoming infrared energy. The microprocessor and network interface module execute a low-power sleep mode until a motion detection event. A hardware interrupt mechanism may be used to wake the microprocessor and network interface module from the sleep modes.

The motion or event detector 702a, 722 and 702c may be based on other technologies such as a laser-based "trip-line," vibration sensors, RF based motion sensors, optically-based motion sensors or sound sensors. Each of these types of sensors is aimed at detecting an event of interest that is to trigger further sensing by way of illuminated imaging.

The illustrative illuminator 708a, 702b, and 724 utilizes an infrared LED or other modern, low-power illumination technology that generates the necessary light output. The LED or laser-based illumination may operate in visible or infrared bands depending on the imaging application. The microcontroller 704 manages activation of the illumination so that power consumption is minimized. The techniques for minimizing power consumption include minimizing duty cycle by both the total time the illumination is on, and by using PWM to modulate total power to the system.

The illustrative solar panel 710 provides electricity converted from solar energy to the charge circuit 712. The charge circuit 712 manages charging the battery 714 from the available solar energy and distributes power to the other hardware components. Additionally, the system may operate using an external non-solar power energy source.

The remote sensing device 720 may also incorporate a mechanical device or other such devices for changing the camera's field of view within a larger field of regard. Each motion or event detector 702a, 722 and 702c or illuminator 708a, 702b, and 724 may be associated with a position of the camera within this larger field of regard. A field of regard includes the area covered by the sensor or detector when pointing to all mechanically possible positions. When a sense-event message such as the detection message is received by the remote sensing device, the camera may then adjust its field of view within the field of regard that is associated with one of the motion or event detector 702a, 722 and 702c or illuminator 708a, 702b, and 724. This mechanism further extends the total field of coverage of the surveillance system substantially.

In the illustrative embodiments of the remote system presented herein, a networked system includes one or more endpoints and a camera system with node-capable viewing the desired field of regard. Each endpoint may include a solar panel, solar charging system, internal battery, low-power wireless communications interface, microcontroller, daylight sensor, motion detection sensor such as PIR, or low-power illumination module such as LED.

Referring to FIGS. 8A and 8B, there is shown an illustrative autonomous method for managing and controlling the remote sensing devices. The method is initiated at block 802 where the smartphone operating system boot sequence is modified so that the operating system will automatically start from a full unpowered state, i.e. battery dead state, without requiring a user screen interaction. Alternatively, the microcontroller turns on the smartphone. More specifically, smartphones include a bootloader program that is responsible for starting the operating system, as well as some peripherals such as the battery charging system. The bootloader program is capable of detecting when power is applied to the phone via the USB port. Normally phones require an external user input, e.g. press power button, in order to boot the operating system. In the illustrative method presented herein, the bootloader program is modified so that a power input will start the operating system at any time power is available, without any user input.

This automatic boot from poweroff is achieved as follows: When the device is fully powered off, pressing the power key or applying power via the USB cable will trigger a section of code (called "u-boot"). This code is part of the Android operating system framework adapted to a specific phone. The u-boot code determines the reason for power up. If the reason was the power key press, a normal Android boot is initiated. If the USB was the reason, the then operating system normally boots to a "charge only" mode. A modification to this "u-boot" code causes the phone to boot to Android no matter the reason for the power up (i.e., in both USB-connect and button-press cases).

In some Android systems, a "power off" (via power button) does not completely power down the phone, but instead places Android into a low power state. In this case, the u-boot logic does not execute when the power-button or USB input is triggered. Instead, a system-level executable is in control of the phone. This system level executable also includes logic for entering a "charge-only" state upon USB input. The present invention also modifies the logic in this system-level executable so that the USB input will boot Android, avoiding a "charge only" state.

The specific location and mechanism for the operating system/phone to decide whether to boot to Android or remain in a "charge only" state may vary from specific phone hardware platform. However, the basic mechanism can be found and one skilled in the art can see that that logic can be similarly modified even in hardware platforms that partition the logic differently. For example, in an alternate embodiment, the smartphone may be modified to connect the user power switch to the microcontroller, and the microcontroller firmware may then control the user power switch to turn on the smartphone, thereby eliminating the need to modify the bootloader.

A second part of the present invention relating to automatic start of the application includes automatically launching the MNode application upon operating system reboot. This is achieved by the MNodeApp registering to have itself launched when the Android "ACTION_BOOT_COMPLETED" intent is broadcast (when the Android boot process is complete).

The method then proceeds to block 804 where a software module is installed on the remote sensing device. More particularly, a remote sensing device software module or "application" is installed and executed on the smartphone. The remote sensing device software module provides all required functions for operation as a presented herein.

The method then proceeds to block 806 where the remote sensing software module registers with the smartphone operating system in such a way that the remote sensing module will be automatically started anytime the operating system is started.

At block 808, the method then proceed with the remote sensing software module initiating wireless communications by opening an illustrative built-in cellular network communications channel, an illustrative built-in Wi-Fi network communications channel, or other such communications channel according to the configuration defined by the smartphone and the remote sensing software module.

In operation, the MNode is configured by an end user or manufacturer to utilize either a Wi-Fi or cellular network. This is achieved by the user connecting to the system via USB2 or Bluetooth. This interface allows the user to select the Wi-Fi or cellular interface, and to configure the interface, e.g. enter Wi-Fi SSID/Passwords.

The method then proceeds to block 810 where the remote sensing software module is configured to automatically register the remote sensing device with the illustrative web application server over a Local Area Network with the illustrative Wi-Fi network communications channel. Additionally, the illustrative remote sensing software module is configured to automatically register the remote sensing device over a Wide Area Network, such as the Internet, with the illustrative built-in cellular communications channel. The registration process establishes communications between the remote sensing software module and the selected web application server.

Upon deployment, the MNode uses the designated network to communicate to the web application server which is running at a fixed IP address. This allows the MNode to become part of the monitoring network without having a fixed IP address, and this ability to operate without the MNode fixed IP is critical to operating on a cellular network. This architecture also has the additional advantage of not requiring any firewall or router configuration modifications in order for the MNode to operate on LANs that have a firewall/router between the LAN on the Internet.

Once registered with the WebApp Server, the MNode requests a configuration to be downloaded that includes the program parameters for the MNodeApp including: when to trigger pictures, when to upload data, how often or under what conditions to log data, which events to notify user, etc.

At block 812, the remote sensing software module requests a configuration from the web application server, which controls the operation of the remote sensing software module including logging of data and images, alerts and notifications, and periodic upload of data to at least one web application server.

One illustrative programmable parameter of the MNode includes the "heartbeat" period, which is the length of time the MNode will wait to contact the WebApp server again. Since the MNode is not required to have a fixed IP address, the architecture is that the MNode contacts the WebApp server in order for any communications to take place.

The heartbeat is a programmable schedule at which the MNode contacts the WebApp server in order to receive messages pending from the WebApp server, and to upload any data pending to be uploaded from MNode to server. In typical remote sensing systems, the server contacts the remote nodes to establish communications. The heartbeat architecture of the present invention provides several advantages over prior art including: (a) does not require remote node to have fixed IP address or any other fixed address, (b) simplifies the WebApp server in not having to maintain list of active devices until those devices first contact the WebApp, (c) provides enhanced security from denial of service and other network level attacks on the remote node.

The heartbeat schedule in the MNode is programmable, and includes two "levels" of communications frequency. A first frequency ("short heartbeat") is a higher frequency of communications and is used once the MNode contacts the WebApp server and finds a message pending. This short heartbeat is used until a timeout period has been reached ("heartbeat timeout"), at which time the MNode reverts to a second longer heartbeat frequency ("long heartbeat"). This scheme allows a beneficial tradeoff between system responsiveness and power consumption; the long heartbeat allows lower system duty cycles, while the short heartbeat allows responsive user interaction with the system. In an alternative embodiment, these heartbeats may be modified dynamically based on time of day, user interaction, or other factors, in order to further optimize the tradeoff between power consumption and system responsiveness.

Another known problem with distributed and networked systems includes "registering" the device with the server or other nodes, so that that new device becomes known to the system. This registration may also include initialization procedures and data that may be required for the new remote node to properly operate as part of the network. Traditionally, this is performed by an external process for the server to know about the node, such as entering a serial number or network address. In the present invention, the "reverse" communications architecture along with the "heartbeat" mechanism, are used to simplify the provisioning. An MNode coming from the factory, or from a virgin state, transitions to an active state by sensing a power input (or other means). Once in this active state, the MNode will use the heartbeat mechanism described above to contact the server. If this is the first time the MNode has contacted the web application server, a "provisioning process" is triggered, whereby the web application server provisions that device into the network and thereby enables subsequent communications and management of the node by the web application server. This method of automated provisioning simplifies the process and removes the burden from the user of configuring a node into the network.

Once the web application server initiates the provisioning process with the newly discovered MNode, additional provisioning steps can easily be included such as updating the MNode with the latest firmware revisions, and configuring the device to the proper initial state.

The method then proceeds to block 814 where the remote sensing software module disposed on the smartphone, controller, or the combination thereof determines whether to enter a "hibernate" mode or state. In the hibernate state, the smartphone phone shuts itself off and the illustrative controller firmware module removes power input from the smartphone. The hibernate mode includes an extreme low power state that can be entered and exited via user input from the USB2. By way of example and not of limitation, the hibernate mode is used to ship the unit from the factory to the user so that battery is not significantly discharged during this transition when no power input is available.

By way of example and not of limitation, the microcontroller issues a "reboot -p" command to the phone via the ADB shell connection; this powers off the smartphone. The microprocessor then cuts power to the smartphone and then enters sleep mode itself, but ensures that the USART stays active. For example, every eight seconds the smartphone wakes up via a watchdog alarm and checks the serial port for the wakeup command, and checks if power was applied, also triggering a wakeup. When the appropriate instruction is received, the microprocessor restores power to the phone. By way of example and not of limitation, a "Boot to Android" firmware mode may be installed in the phone, which causes the phone to boot up and start running the illustrative MNodeApp. Alternatively, the microcontroller controls the phone power switch in order to boot the phone and start the MNodeApp. Subsequently, the microprocessor resumes normal operations.

The method then proceeds to decision diamond 816, where a decision is made regarding thermal management. More specifically, remote battery/solar powered camera/monitoring systems may need to provide heating in order to maintain internal electronics above minimum operating temperatures in the face of lower external ambient temperatures. Heating can represent a significant power requirement for solar/battery powered systems in colder climates. A "thermal battery" technique is used to minimize overall energy consumption while maintaining the required minimum operating temperatures for internal electronics. The remote sensing device includes a method of thermal management that takes advantage of the diurnal cycle and utilizes a thermally insulated electronics enclosure to store thermal energy during periods when solar charging power is more abundant.

This stored thermal energy enables maintenance of the internal electronics above minimum operating temperature at a lower overall system energy consumption than would otherwise be possible.

The illustrative algorithm for thermal management uses the internal electronics to measure input power from the solar charging system, the current battery states, the outside ambient temperature, and weather forecast. If the forecast calls for outside ambient temperatures significantly below the minimum operating temperature of the electronics, and the solar charging system is providing excess power above what is needed to maintain the batteries at desired operating levels, then the thermal management algorithm will "divert" some of this input electricity to the heating system. The heating system will thereby bring the internal temperature above the minimum operating temperature, even up to the maximum operating temperature of the electronics.

With this thermal management method, on days where a "cold night" is coming, any excess solar power input is converted to thermal energy and "stored" in the enclosure/electronics by virtue of the insulated enclosure. The system can be further enhanced by increasing the overall thermal mass of the system by including in the enclosure design, significant mass of metal, or other thermally conductive material, to further "store" the thermal energy.

As the diurnal cycle progresses and the ambient external temperature drops, the system will have reduced need to provide heating of the electronics due to thermal mass of the system. This reduces the overall power requirement for the system (batteries, solar panel capacity).

The illustrative thermal management system may be further enhanced by using an electrically-based cooling system (such as a peltier device) to maintain internal electronics below maximum operating temperatures. In this case, the maximum cooling requirement will coincide with the daytime and maximum solar capture period. However, the algorithm can be modified in this case to use any excess solar input power to cool the system below the required maximum upper temperature, and store the negative thermal energy to provide "carry over" cooling during periods when there is no excess solar input energy.

The method then proceeds to decision diamond 818, where a determination of frequency logging is made based on bandwidth and power consumption. A key parameter in a remote telemetry system is the utilization of both power and bandwidth for communications. Many aspects, such as the data logging frequency, are user-programmable and include a software function for providing automated bandwidth and power estimation in order to guide user expectations and programming of the system.

In the illustrative embodiment, the bandwidth estimator includes a programmable upload parameter. This parameter determines how often logged data is uploaded to the server. The system also includes user-programmable data logging statements. The data logging statements include the type of data to be logged (e.g., analog value, image) and the frequency of logging. The bandwidth estimator first calculates the amount of data that is expected to be logged during a given bandwidth usage period (e.g., month). The bandwidth estimator then inspects the currently programmed upload frequency. These values are combined to provide an estimate of the network bandwidth required during a given bandwidth usage period.

Some data logging can be programmed to occur based on external events (e.g., capture image when there is motion detected). In this case, the bandwidth estimator uses a fixed background frequency for that type of event (X times per day). This estimate then generates an expected amount of event-driven logged data that can be added to the scheduled data estimate.

The normal operation of the device is to remain in "sleep" mode unless there is an event-driven action (e.g., data logging) or a schedule-driven event (e.g., logged data). Power consumption in sleep mode is significantly less than when the unit is awake to process an event. The power estimator also operates on the scheduled and event-driven program settings of the device. Each scheduled or event-driven program is assigned a "processing time" required to take that action. For example, the time to wake up, take and store an image, go back to sleep. The power consumption of the device during this operation is known to the system for both sleep and "processing" states. There may be different power consumption values for different processing states (e.g., taking picture vs. logging data value). The total time required for all programmed and event-driven actions is compared to a given time period (e.g., per hour) to determine a "duty cycle." This duty cycle represents the percent of time the system spends at each "power consumption level." Thus, the total power consumption is estimated for the given programmed regime.

The method then proceeds to decision diamond 820 where the alarm verification process is initiated. Alarm verification refers to the process of having an alarm associated with a first sensor, e.g. motion detector, triggered by having detected a particular event, e.g. motion, and then proceeds to "verify" the event by using another sensor, e.g. a camera, to take a picture at the same time that the alarm was triggered. The illustrative example of alarm verification in a perimeter security system provides automatic alarm verification without requiring user communication or network traffic. More specifically, the MNode may be configured to have at least one "perimeter intrusion sensors," such as passive infrared (PIR), infrared (IR) beams, fence-line vibration sensors, or other sensor that is capable of detection an event of interest such as heat, motion, or sound.

More generally, event evaluation is performed at decision diamond 822. Events are conditions that are periodically evaluated and result in action or alert. An action refers to starting or stopping a process. An alert refers to a notification that is sent to a particular user, group or autonomous monitoring entity. Event evaluation entails reading the most current sensor values, looking at programmed event/alarm specifications, determining the true events and/or alarms associated therewith and taking the prescribed actions. In this illustrative embodiment, the alarm verification is a species or type of the more general event evaluation process.

For example, when the MNode receives the signal over the wireless sensor network from any of the attached perimeter intrusion sensors, it automatically collects one or more images or video clips of the region covered by the intrusion sensor. The illustrative collected images are configured to be processed by the MNode software application to detect visual objects of interest, e.g. human or vehicle. The MNode software application may use any of a number of known algorithms for video motion detection, object detection, or other visual event detection, by means of the powerful phone processor, in order to carry out this visual detection onboard the phone. A positive detection results in a confirmed "alarm" that is then communicated to the user as an intrusion alarm. A lack of detection indicates that the intrusion sensor provided a false alarm.

Typical intrusion sensors, such as PIR, often have very high "false alarm" rates, i.e. a signal when there is no event of interest. This method of automatic visual alarm verification or event evaluation reduces the false alarms that the system user sees. By performing the processing for this event evaluation or alarm verification on the MNode, the process also reduces network traffic by avoiding sending of alarms or images that have not been verified.

Referring now to FIG. 9A, there is shown a perspective view of an illustrative enclosure. In FIG. 9B there is shown a top view of the illustrative enclosure. The illustrative enclosure 902 is configured to receive a smartphone 904 that is electrically coupled to a smartphone connection 906. A microcontroller 908 is proximate to the smartphone 904 and two auxiliary batteries 910. The enclosure also includes a first connector 912 for power input from an illustrative solar panel. Additionally, the enclosure includes a second connector 914 that provides a USB for a hardwire connection to the microcontroller 908.

The auxiliary battery 910 is electrically coupled to the power management module and illustrative solar panels (not shown). The solar panels charge the auxiliary battery 910, which then charges the battery in smartphone 904.

The enclosure 902 also houses the thermistor, cooler, and heater elements. This enclosure seals these components from the environment and provides an appropriate thermal environment which can be temperature controlled to maintain internal temperatures within allowable range in the face of ambient temperature fluctuations. The enclosure 902 is fabricated from materials that do not attenuate RF signals in the bands used by cellular, Wi-Fi, Bluetooth, NFC, and wireless sensor networks.

Additionally, the enclosure 902 incorporates one or more optically transparent windows 916. The smartphone 904 is mounted in the enclosure 902 such that the field of view 918 passes through the enclosure window 916.

An additional optional camera or other such sensor may be mounted in the same enclosure or a separate enclosure 902. The optional camera or sensor communicates with the smartphone via wireless (Wi-Fi, Bluetooth) or USB. The illustrative sensor includes a wireless thermal infrared (TIR) or a passive infrared (PIR) sensor that can also be combined with a remote wireless illumination node. The illumination node can be powered by a battery, a solar panel, or the combination thereof, as described herein. The illumination node is a low power node that illuminates the vicinity surrounding the node location.

Referring to FIG. 10, there is shown a screenshot for an illustrative dashboard that logs data for the remote sensing system described above. The dashboard 1000 includes an image or video 1002 captured by a camera associated with the remote sensing device. In addition to the location 1004 of the remote sensing device being provided, the dashboard 1000 also includes power information 1006, device and network information 1008. Additionally, various system alarms 1010 are presented on the right hand side of the user interface. At the bottom of the page, a chronological data log 1012 is provided that includes various annotations and recordings.

The illustrative remote sensing device, system, and method described a smartphone programmed for remote operation that is housed in an environmentally controlled housing. The illustrative smartphone includes a microprocessor, non-volatile storage, an integrated camera, an integrated and/or modular battery, and at least one wired or wireless interfaces such as a point-to-point interface, LAN interface, a WAN interface, or any combination thereof.

Additionally, the remote sensors may be connected via the wired or wireless interfaces. Illustrative remote sensors include transducers and smart sensors. These remote sensors may provide input or output of analog or discrete values via connected transducers, switches, relays, and other such communication paths.

The remote sensing system also optionally includes one or more batteries that are housed in the environmentally controlled housing. An optional input for external power (from a mains, or solar panel or other source) is managed by a battery charging circuit which recharges both the phone and any auxiliary batteries to maintain charge levels from external power inputs.

In yet another illustrative embodiment, the remote sensing system includes a networked system comprising one or more endpoints and a camera system node capable viewing the desired field of regard. The endpoints each comprise a solar panel, solar charging system, internal battery, low-power wireless communications interface, microcontroller, daylight sensor, motion detection sensor (such as PIR), and a low-power illumination module, such as LED.

For example, the endpoint collects power from the solar panel and stores it in the battery. The battery provides power to the other system elements. The motion-detection sensor signals the microprocessor when motion is detected. Upon motion detection, the microprocessor sends a message over the low-power wireless communications interface to the camera system. Upon receiving the message, the camera initiates an image capture of either still images or video sequence. If the endpoint's daylight sensor indicates that it is dark, then the endpoint illuminates its area using the illumination module so that the camera captures an illuminate image.

In a further illustrative embodiment, the remote sensing system includes a camera system node that includes a low-power wireless communications interface enabling communication between the camera and the endpoints. The camera system may comprise a fixed camera or a moveable camera (pan-tilt zoom).

Additionally, an illustrative remote sensing method is embodied in a remote sensing application that communicates with the associated sensors/cameras of the remote sensing system. The illustrative software application may be configured based on the presence of, and/or sensed values from, the attached sensors. The illustrative software application and method handles the reading of the attached sensors/cameras, storage and timestamp of captured data, local data processing based on programmed configuration, issuing alarms to remote users per the configuration, uploading captured data to remote site per the programmed configuration, and controlling sensors per the remote commands or programmed configuration.

An illustrative apparatus is also described that includes a smartphone housed in an environmentally controlled housing that includes at least one sensor for detecting internal temperature of the enclosed phone and electronics, a cooling device for cooling the internal enclosure and electronics (e.g. as a Peltier cooler), a heating device for heating the internal enclosure and electronics (e.g. as a Peltier or resistive heater), a comparator circuit for comparing sensed temperature to stored desired min/max temperature ranges, and controlling heater/cooler devices to maintain an internal temperature within required ranges.

The remote sensing system described above satisfies a plurality of key requirements that enables remote sensing system to support a variety of different features. The feature may be deployed at a low cost, consume low power, and have ability to support the local storage of data, operate on familiar software development platforms, provide multiples modes of communication, support an integrated data framework, and support user mobility.

Low cost is a key requirement because a given application may require hundreds or thousands of remote monitoring sites to implement an application. Total system cost—including hardware, software development, communications, installation, and maintenance—are critical to the applicability of the solution.

Low power is also a key requirement. Power supplies—including solar, batteries, and cabling—all grow the size, weight, and cost as a function of the power requirements of the device.

Another key requirement for remote sensing is the ability to provide local processing of data, because remote communications may be intermittent, have variable latencies, and incur communications costs. Some remote monitoring and/or control applications require data to be logged or acted upon within a fixed interval of time. Therefore, there is a requirement that the remote sensing system have the ability to perform some processing of the IO data independent of any wide area communications or other system elements. Local processing of data also allows the sensing node to act based in sensed values, for example, only record images when motion sensor is triggered. Visual alarm verification onboard the smartphone can significantly reduce mobile communications costs, providing a significant commercial advantage.

An ability to provide local storage of data is another requirement for remote sensing. Remote communications to the sensing system may be intermittent. To ensure continuous monitoring and collection of data it is necessary for the remote sensing system to have local storage of data. Since a remote sensing system may collect many channels of data over long periods of time, it is beneficial to have a substantial amount of local storage capability.

Yet another requirement for remote sensing is a simple, flexible, well-known software development platform because some applications require specific logic to operate on the remote sensing device to implement the required data collection, control, or alarming functions. In order to facilitate development of this logic at the lowest cost, it would be beneficial to support a remote sensing platform that utilizes a widely available software platform for development and deployment of applications.

Multiple modes of communication are another requirement for remote sensing. In order to provide communications of data from the remote site to the user or central operations, and in order to provide remote control of devices managed by the remote sensing system, a communications capability is required as part of the remote sensing system. For reliability, and ease of deployment it would be beneficial to provide multiple modes of communication supported (e.g., Wi-Fi, Cellular, Satellite). Wireless communications are strongly preferred over wired in order to achieve simplicity and low cost installation and maintenance.

A further remote sensing requirement includes integrated analog, digital, and image and video data. Modern applications require both analog and digital IO capabilities, as well as still and video data. To achieve the goals of simplicity and low cost, it is necessary to have a single integrated platform that can support the IO and processing of analog, digital IO, as well as video and still imagery.

Furthermore, mobility is another requirement of remote sensing because some applications (e.g. transportation) require remote sensing system to move with the device (vehicle) or environment being sensed. It would therefore be beneficial for the remote sensing system to be capable of being used in fixed applications, mobile applications, or any combination thereof.

It is to be understood that the detailed description of illustrative embodiments are provided for illustrative purposes. The scope of the claims is not limited to these specific embodiments or examples. Therefore, various elements, details, execution of any methods, and uses can differ from those just described, or be expanded on or implemented using technologies not yet commercially viable, and yet still be within the inventive concepts of the present disclosure. The scope of the invention is determined by the following claims and their legal equivalents.

What is claimed:

1. A remote illumination and detection method comprising,
    enabling each of a plurality of detectors to generate a detection message when motion is detected by a detector, wherein the detector includes a first wireless communications module;
    a detection field proximate to each of the plurality of detectors, wherein the detection message is generated when motion is detected within the detection field proximate to each of the plurality of detectors;
    wirelessly transmitting the detection message to a remote sensing device that includes a camera having a field of view of the plurality of detectors and the corresponding detection field associated with each of the plurality of detectors, and a second wireless communications module corresponding to the remote sensing device that communicates with the first wireless communications module associated with each of the plurality of detectors;
    generating an illumination instruction, at the remote sensing device, when the remote sensing device receives the detection message from one of the plurality of detectors;
    wirelessly transmitting the illumination instruction to an illuminator that is communicatively coupled to a third wireless communications module, wherein the third wireless communications module is communicatively coupled to the second communication module associated with the remote sensing device, the illuminator having an illumination area that includes the detection field corresponding to one of the plurality of detectors, wherein the illumination area is within the field of view of the camera; and
    illuminating the illumination area when motion is detected by one of the plurality of detectors and the illumination instruction is received by the illuminator.

2. The remote illumination and detection method of claim 1 further comprising,
    housing one detector of the plurality of detectors and the illuminator in an illumination and detection node, in which the first wireless communication module and the third wireless communications module are a same wireless communication module;
    wirelessly communicating the detection message from the illumination and detection node to the remote sensing device;
    illuminating the area of the illuminator when the illumination instruction communicated by the remote sensing device is received by the illumination and detection node.

3. The remote illumination and detection method of claim 1 further comprising:

housing the illuminator in a remote illuminator node, wherein the illuminator illuminates the illumination area associated with the illuminator; and receiving, by the remote illuminator node, the illumination instruction generated by the remote sensing device.

4. The remote illumination and detection method of claim 1 further comprising, housing one of the plurality of detectors in a remote detection node;

detecting motion, by the detector housed in the remote detection node, in a detection area within the field of view;

generating the detection message;

wirelessly communicating the detection message to the remote sensing device; and illuminating the illumination area associated with the detection area when the detection message generated by the detector housed in the remote detection node is received by the remote sensing device, which then communicates the illumination instruction to the remote illuminator node associated with the illumination area.

5. The remote illumination and detection method of claim 1 wherein the illuminator includes a low power infrared or visible LED output.

6. The remote illumination and detection method of claim 1 wherein each of the plurality of detectors includes an infrared detector.

7. The remote illumination and detection method of claim 1 further comprising:

powering the detector housed in the remote detection node with a battery; and charging the battery with a solar panel electrically coupled to the battery.

8. A remote illumination and detection node comprising, an illumination housing;

a wireless network interface module configured to be communicatively coupled to a remote sensing device that further includes a camera having a field of view;

a detector having a detection field proximate to the detector, wherein the detector configured to detect motion in the detection field, wherein the field of view includes the detection field;

a processor configured to transmit a detection message to the remote sensing device, when motion is detected by the detector in the detection field; and an illuminator operatively coupled to the processor, wherein the illuminator is configured to illuminate an illumination area when the processor receives an illumination instruction to illuminate the illumination area, wherein the illumination area includes the detection field.

9. The remote illumination and detection node of claim 8 wherein the remote sensing device includes a smartphone.

10. The remote illumination and detection node of claim 8 wherein the remote sensing device includes a wireless communication module that wirelessly communicates with the remote illumination and detection node.

11. The remote illumination and detection node of claim 8 wherein the detector includes an infrared detector.

12. The remote illumination and detection node of claim 8 wherein the illuminator includes a low power infrared or visible LED output.

13. The remote illumination and detection node of claim 8 further comprising:

a battery configured to power the illuminator, the processor, the detector and the wireless network interface module; and a solar panel electrically coupled to the battery, wherein the solar panel charges the battery.

14. A remote illumination system comprising, a remote detector configured to detect motion in a detection field proximate to the detector and communicate a detection message with a wireless communication protocol, when motion is detected in the detection field of the detector; and a remote sensing device communicatively coupled to the remote detector which applies the wireless communication protocol, wherein the remote sensing device includes a camera having a field of view of the detection field and a remote sensing wireless communications module that receives the detection message from the remote detector, the remote sensing device communicates an illumination instruction to a remote illumination node when the remote sensing device receives the detection message from the remote illumination node, the remote illumination node has an illumination area, the illumination area within the field of view, the illumination area including the associated detection field, the remote illumination node including, a remote illumination housing;

a wireless network interface module configured to be communicatively coupled to the remote sensing device;

a processor configured to receive the illumination instruction to illuminate the illumination area associated with the remote illumination node, when motion is detected by the remote detector associated with the remote illumination node; and an illuminator operatively coupled to the processor, wherein the illuminator is configured to illuminate the illumination area associated with the remote illumination node when the illuminator receives the illumination instruction.

15. The remote illumination system of claim 14 wherein the remote detector includes an infrared detector.

16. The remote illumination system of claim 14 wherein the remote illuminator node includes a low power infrared or visible LED output.

17. The remote illumination system of claim 14 further comprising:

a battery configured to power the illuminator, the processor, the detector and the wireless network interface module; and a solar panel electrically coupled to the battery, wherein the solar panel charges the battery.

18. A remote illumination system comprising, a remote illuminator that illuminates an illumination area when the remote illuminator receives an illumination message;

a remote sensing device communicatively coupled to the remote illuminator node, wherein the remote sensing device includes a camera having a field of view of the illumination area and a remote sensing wireless communications module;

a remote detection node that includes, a remote detection node housing;

a wireless network interface module configured to be communicatively coupled to the remote sensing device;

a detector operatively coupled to a processor, the detector configured to detect motion in a detection field proximate to the detector and generate a detection message when motion is detected, wherein the illumination area includes the detection field;

the processor operatively coupled to the detector, wherein the processor is configured to transmit the detection message that is communicated wirelessly to the remote sensing device;

a battery configured to power the detector, the processor and the wireless network interface module; and the remote illuminator configured to illuminate the illumination area when the detection message generated by the remote detection node is received by the remote sensing device, which then communicates the illumination instruction to the remote illuminator node.

19. The remote illumination system of claim 18 wherein the remote illuminator includes a low power infrared or visible LED output.

20. The remote illumination system of claim 18 wherein the remote detection node includes an infrared detector.

21. The remote illumination system of claim 18 further comprising:

a battery configured to power the illuminator, the processor, the detector and the wireless network interface module; and a solar panel electrically coupled to the battery, wherein the solar panel charges the battery.

* * * * *